United States Patent
Dezawa et al.

(10) Patent No.: US 10,196,605 B2
(45) Date of Patent: *Feb. 5, 2019

(54) TREATMENT OF CNS DISORDERS USING DESCENDANTS OF MSCS EXPRESSING AN EXOGENOUS NOTCH INTRACELLULAR DOMAIN

(71) Applicant: SanBio, Inc., Mountain View, CA (US)

(72) Inventors: Mari Dezawa, Kyoto (JP); Hajime Sawada, Yokusuka (JP); Hiroshi Kanno, Yokusuka (JP); Masahiko Takano, Yokusuka (JP)

(73) Assignee: SanBio, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/192,671

(22) Filed: Jun. 24, 2016

(65) Prior Publication Data

US 2016/0304835 A1    Oct. 20, 2016

Related U.S. Application Data

(63) Continuation of application No. 13/733,510, filed on Jan. 3, 2013, now Pat. No. 9,399,046, which is a continuation of application No. 12/584,657, filed on Sep. 10, 2009, now Pat. No. 8,361,456, which is a continuation of application No. 10/503,816, filed as application No. PCT/JP03/01260 on Feb. 6, 2003, now Pat. No. 7,682,825.

(30) Foreign Application Priority Data

Feb. 6, 2002 (JP) ................. 2002-030003

(51) Int. Cl.
| | |
|---|---|
| *A61K 35/28* | (2015.01) |
| *C12N 5/0793* | (2010.01) |
| *C12N 5/077* | (2010.01) |
| *A61K 35/30* | (2015.01) |
| *A61K 9/00* | (2006.01) |
| *C12N 5/079* | (2010.01) |
| *A61K 35/12* | (2015.01) |
| *C12N 5/0775* | (2010.01) |

(52) U.S. Cl.
CPC ............ *C12N 5/0619* (2013.01); *A61K 35/28* (2013.01); *A61K 35/30* (2013.01); *C12N 5/0658* (2013.01); *A61K 9/0085* (2013.01); *A61K 2035/124* (2013.01); *C12N 5/0618* (2013.01); *C12N 5/0663* (2013.01); *C12N 2501/42* (2013.01); *C12N 2502/1358* (2013.01); *C12N 2506/1353* (2013.01); *C12N 2510/00* (2013.01)

(58) Field of Classification Search
CPC ............................. C12N 5/0619; A61K 35/28
See application file for complete search history.

(56) References Cited

U.S. PATENT DOCUMENTS

| | | |
|---|---|---|
| 5,226,914 A | 7/1993 | Caplan et al. |
| 5,591,625 A | 1/1997 | Gerson et al. |
| 5,780,300 A | 7/1998 | Artavanis Tsakonas et al. |
| 5,854,004 A | 12/1998 | Czernilofsky et al. |
| 6,555,374 B1 | 4/2003 | Gimble et al. |
| 7,015,037 B1 | 3/2006 | Furcht et al. |
| 7,229,827 B2 | 6/2007 | Kim et al. |
| 7,682,825 B2 | 3/2010 | Dezawa et al. |
| 8,092,792 B2 | 1/2012 | Dezawa et al. |
| 8,133,725 B2 | 3/2012 | Dezawa et al. |
| 9,399,046 B2 | 7/2016 | Dezawa et al. |
| 2001/0044122 A1 | 11/2001 | Buck et al. |
| 2002/0146821 A1 | 10/2002 | Sanchez Ramos et al. |
| 2006/0216276 A1 | 9/2006 | Dezawa et al. |
| 2011/0136114 A1 | 6/2011 | Case |
| 2013/0209428 A1 | 8/2013 | Dezawa et al. |

FOREIGN PATENT DOCUMENTS

| | | |
|---|---|---|
| WO | WO 1999/056759 | 11/1999 |
| WO | WO 2000/017326 | 3/2000 |
| WO | WO 2001/022978 | 4/2001 |
| WO | WO 2001/059072 | 8/2001 |
| WO | WO 2009/073180 | 6/2009 |

OTHER PUBLICATIONS

Nguyen et al (Advanced Drug Delivery Reviews, p. 1-12. 2014) (Year: 2014).*
American Heritage Dictionary, Second College Edition, definitions for "treat" and "treatment", p. 1290.
Bain, et al., "Embryonic Stem Cells Express Neuronal Properties In Vitro," Developmental Biology 168:342-357 (1995).
Barker, et al., "Neural Transplantation Therapies for Parkinson's and Huntington's Diseases," Drug Discov Today 6:575-582 (2001).
Bourque, et al., "GDNF Enhances the Synaptic Efficacy of Dopaminergic Neurons in Culture," Eur J Neurosci. 12(9):3172-3180 (2000).

(Continued)

*Primary Examiner* — Anoop K Singh
*Assistant Examiner* — Magdalene K Sgagias
(74) *Attorney, Agent, or Firm* — Levine Bagade Han LLP

(57) ABSTRACT

There is provided a method of inducing differentiation of bone marrow stromal cells to neural cells or skeletal muscle cells by introduction of a Notch gene. Specifically, the invention provides a method of inducing differentiation of bone marrow stromal cells to neural cells or skeletal muscle cells in vitro, which method comprises introducing a Notch gene and/or a Notch signaling related gene into the cells, wherein the finally obtained differentiated cells are the result of cell division of the bone marrow stromal cells into which the Notch gene and/or Notch signaling related gene have been introduced. The invention also provides a method of inducing further differentiation of the differentiation-induced neural cells to dopaminergic neurons or acetylcholinergic neurons. The invention yet further provides a treatment method for neurodegenerative and skeletal muscle degenerative diseases which employs neural precursor cells, neural cells or skeletal muscle cells produced by the method of the invention.

10 Claims, 24 Drawing Sheets

(56) References Cited

OTHER PUBLICATIONS

Carvey, et al., "A Clonal Line of Mesencephalic Progenitor Cells Converted to Dopamine Neurons by Hematopoietic Cytokines: A Source of Cells for Transplantation in Parkinson's Disease," Exp. Neurol 171:98-108 (2001).
Chopp et al., "Spinal Cord Injury in Rat: Treatment With Bone Marrow Stromal Cell Transplantation," Neurareport 11(13):3001-3005 (2000).
Conget, et al., "Phenotypical and Functional Properties of Human Bone Marrow Mesenchymal Progenitor Cells," Journal of Cellular Physiology 181:67-73 (1999).
Da Silva Meirelles, et al., "In Search of the In Vivo Identity of Mesenchymal Stem Cells," Stem Cells 26:2287-2299 (2008).
Dahlstrand, et al., "Nestin MRNA Expression Correlates With the Central Nervous System Progenitor Cell State in Many, But Not All, Regions of Developing Central Nervous System," Developmental Brain Research 84:109-129 (1995).
Deng, et al., "In Vitro Differentiation of Human Marrow Stromal Cells Into Early Progenitors of Neural Cells by Conditions That Increase Intracellular Cyclic Amp," Biochem Biophys Res Commun 282:148-152 (2001).
Dezawa, et al., "Specific Induction of Neuronal Cells From Bone Marrow Stromal Cells and Application for Autologous Transplantation," J Clin Invest 113(12):1701-1710 (2004).
Docheva, et al "Human Mensenchymal Stem Cells in Contact With Their Environment: Surface Characteristics and Their Integrin System," J. Cell Mol. Med. 11:21-38 (2007).
Ferrari, et al., "Muscle Regeneration by Bone Marrow-Derived Myogenic Progenitors," Science 279:1528-1530 (1998).
Flax, et al., "Engraftable Human Neural Stem Cells Respond to Development Cues, Replace Neurons, and Express Foreign Genes," Nature Biotechnology 16:1033-1039 (1998).
Glavaski-Joksimovic, et al., "Reversal of Dopaminergic Degeneration in a Parkinsonian Rat Following Micrografting of Human Bone Marrow-Derived Neural Progenitors," Cell Transplant 18:801-814 (2009).
Goldman, et al., "Cell Replacement Therapy in Neurological Disease," Phil. Trans. R. Soc. B 361:1463-1475 (2006).
Hofstetter et al., "Marrow Stromal Cells Form Guiding Strands in the Injured Spinal Cord and Promote Recovery," Proc. Natl. Acad. Sci. 99(4):2199-2204 (2002).
Isacson, "The Production and Use of Cells As Therapeutic Agents in Neurodegenerative Diseases," Lancet Neurol. 2:417-424 (2003).
Itakura, et al., "Transplantation of Neural Tissue Into the Brain, "Neurol Med. Chir 38:756-762 (1998).
Jiang et al., "Pluripotency of Mesenchymal Stem Cells Derived From Adult Marrow," Nature 418:41-49 (2002).
Kalyani, et al., "Spinal Cord Neuronal Precursors Generate Multiple Neuronal Phenotypes in Culture," J. Neurosci 18:7856-7868 (1998).
Katoh, et al., "Notch Signaling in Gastrointestinal Tract (Review)," International Journal of Oncology 30:247-251 (2007).
Kopan, et al., "The Intracellular Domain of Mouse Notch: A Constitutively Activated Repressor of Myogenesis Directed At the Basic Helix-Loop-Helix Region of Myod," Development 120:2385-2396 (1994).
Lindvall, et al., "Stem Cell Therapy for Human Neurodegenerative Disorders—How to Make It Work," Nature Med 10 Suppl S42-550 (2004).
Lu, et al., "Induction of Bone Marrow Stromal Cells to Neurons: Differentiation, Transdifferentiation, or Artifact?" Journal of Neuroscience Research 77:174-191 (2004).
Maier, et al., "Comparative Analysis of the Human and Mouse HEY1 Promoter: Hey Genes Are New Notch Target Genes," Biochemical and Biophysical Research Communications 275:652-660 (2000).
Malatesta, et al., "Isolation of Radial Glial Cells by Fluorescent-Activated Cell Sorting Reveals a Neuronal Lineage," Development 127: 5253-5263 (2000).
Mattson, "Stem Cells As Therapeutics for Neurodegenerative Disorder?" Expert Rev. Neurotherapeutics 1:267-273 (2001).
McDonald, et al., "Transplanted Embryonic Stem Cells Survive, Differentiate, and Promote Recovery in Injured Rat Spinal Card," Nature Medicine 5:1410-1412 (1999).
Neububer et al., "Reevaluation of in Vitro Differentiation Protocols for Bone Marrow Stromal Cells: Disruption of Actin Cytoskeleton Induces Rapid Morphological Changes and Mimics Neuronal Phenotype," Journal of Neuroscience Research 77:192-204 (2004).
Nikkhah, et al., "Platelet-Derived Growth Factor Promotes Survival of Rat and Human Mesencephalic Dopaminergic Neurons in Culture," Exp Brain Res 92:516-523 (1993).
Pagano, et al., "Isolation and Characterization of Neural Stem Cells From the Adult Human Olfactory Bulb," Stem Cells 18:295-300 (2000).
Park, et al., "Transplantation of Neural Stem Cells: Cellular & Gene Therapy for Hypdxic-Ischemic Brain Injury," Yonsei Med J. 41(6);825-835 (2000).
Patrizia, et al., "In Vitro Generation of Muscle Cells From Adult Human Bone Marrow," Database BIOSIS, Abstract from the 43.sup.rd Annual Meeting of the American Society of Hematology Accession No. PREV200200198985 (2001).
Phinney, et al., "Concise Review: Mesenchymal Stem/Multipotent Stromal Cells: The State of Transdifferentiation and Modes of Tissue Repair—Current Views," Stem Cells 25:2896-2902 (2007).
Phinney, et al., "Plastic Adherent Sternal Cells From the Bone Marrow of Commonly Used Strains of Inbred Mice: Variations in Yield, Growth, and Differentiation," Journal of Cellular Biochemistry 72:570-585 (1999).
Rickman, et al., "BDNF and CNTF Enhance the Neuronal Differentiation of Bone Marrow Stromal Cells," Soc. Neurosci.Abstracts 27:58 (2001).
Roybon, et al., "Stem Cell Therapy for Parkinson's Disease; Where Do We Stand?" Cell Tissue Res 318:261-273 (2004).
Schroeder, et al., "Notch Signalling via RBP-J Promotes Myeloid Differentiation," EMBO J 19:2558-2568 (2000).
Sugaya, et al., "Neuroreplacement Therapy and Stem Cell Biology Under Disease Conditions," Cell. Mol. Life. Sci. 60:1891-1902 (2003).
Svendsen, et al., "Long-Term Survival of Human Central Nervous System Progenitor Cells Transplanted Into a Rat Model of Parkinson's Disease," Experimental Neurology 148:135-146 (1997).
Varnum-Finney, et al., "The Notch Ligand, Jagged-1, Influences the Development of Primitive Hematopoietic Precursor Cells," Blood 91:4084-4091 (1998).
Wakitani, et al., "Myogenic Cells Derived From Rat Bone Marrow Mesenchymal Stem Cells Exposed to 5-Azacytidine." Muscle & Nerve 18:1417-1426 (1995).
Weissman, "Translating Stem and Progenitor Cell Biology to the Clinic: Barriers and Opportunities," Science 287:1442-1446 (2000).
Woodbury et al., "Adult Bone Marrow Stromal Stem Cells Express Germline, Ectodermal, Endodermal, and Mesodermal Genes Prior to Neurogenesis," J Neuroscience Research 96:908-917 (2002).
Woodbury et al., "Adult Rat and Human Bone Marrow Stromal Cells Differentiate Into Neurons," Journal of Neuroscience Research 61:364-370 (2000).
Wright et al., "Gene Expression in Human Neural Stem Cells: Effects of Leukemia Inhibitory Factor," Journal of Neurochemistry 86:179-195 (2003).
Yasuhara, et al., "Notch-induced Rat and Human Bone Marrow Stromal Cell Grafts Reduce Ischemic Cell Loss and Ameliorate Behavioral Deficits in Chronic Stroke Animals," Stem Cells and Development 18:1501-1514 (2009).
Steinberg, Gary K. et al., "Clinical Outcomes of Transplanted Modified Bone Marrow-Derived Mesenchymal Stem Cells in Stroke, A Phase 1/2a Study," *Stroke*, 47: 1817-1824, 2016. DOI: 10.1161/STROKEAHA.116.012995.

* cited by examiner

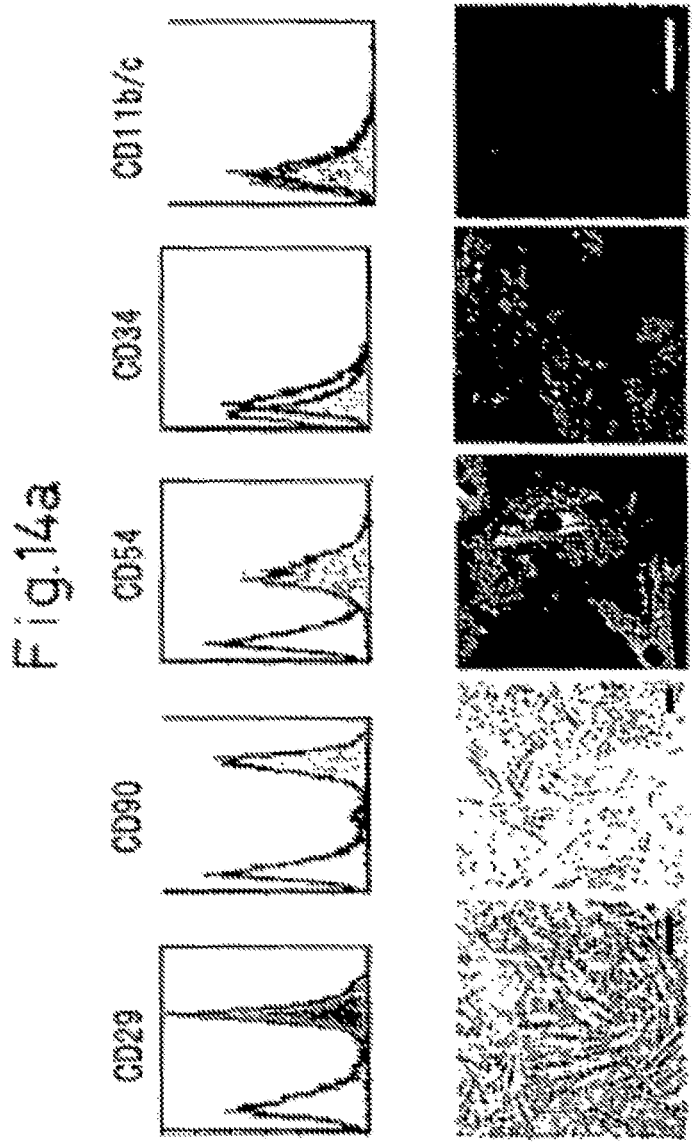

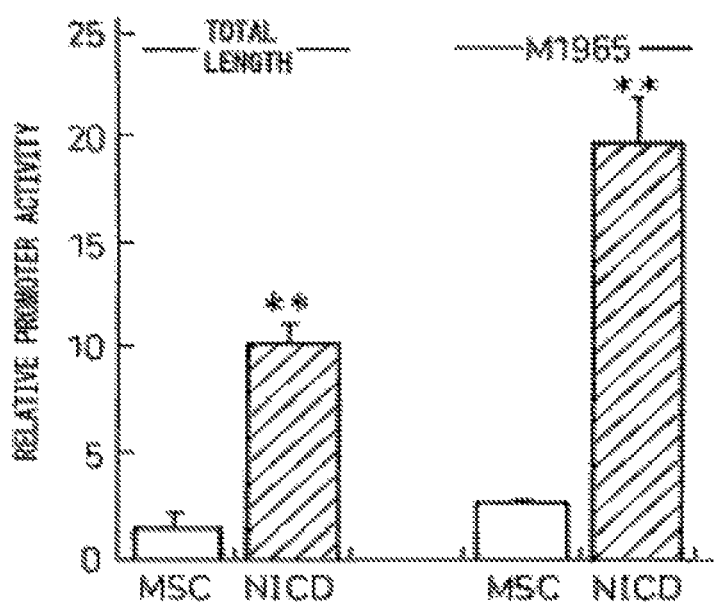

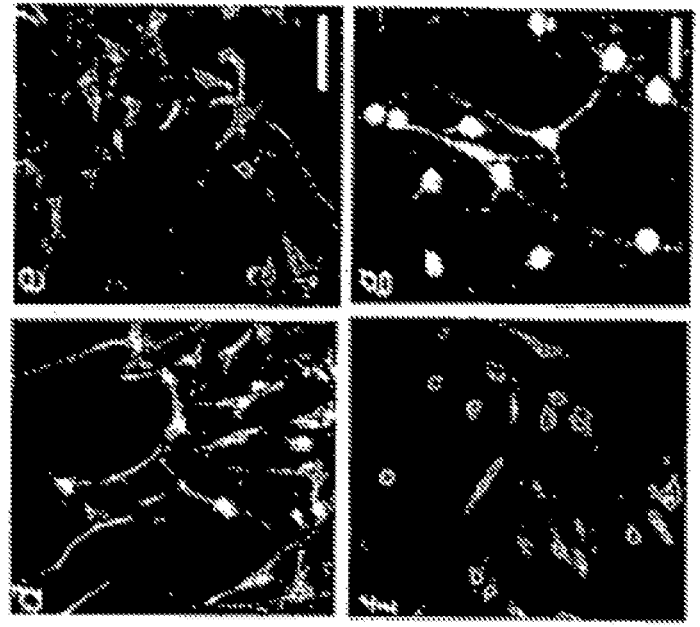
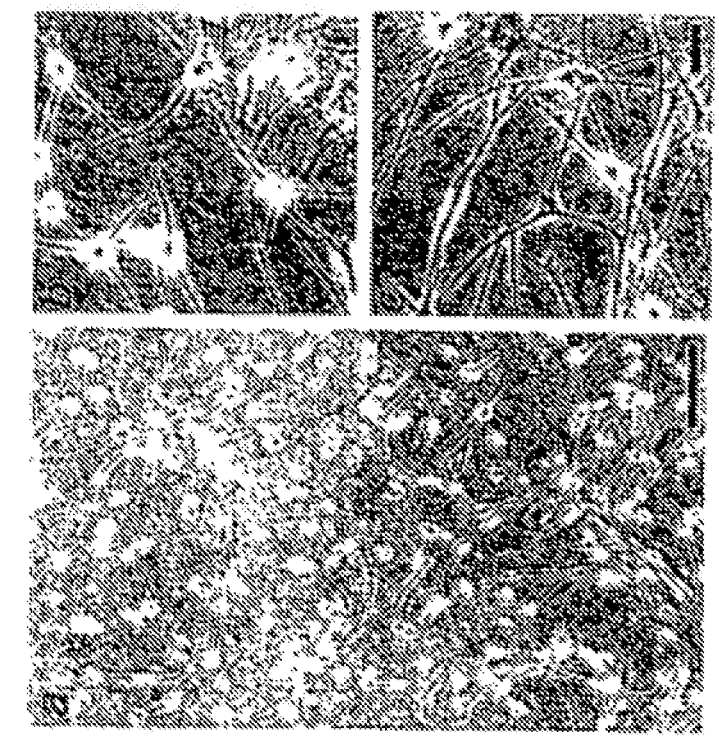

Fig.17h
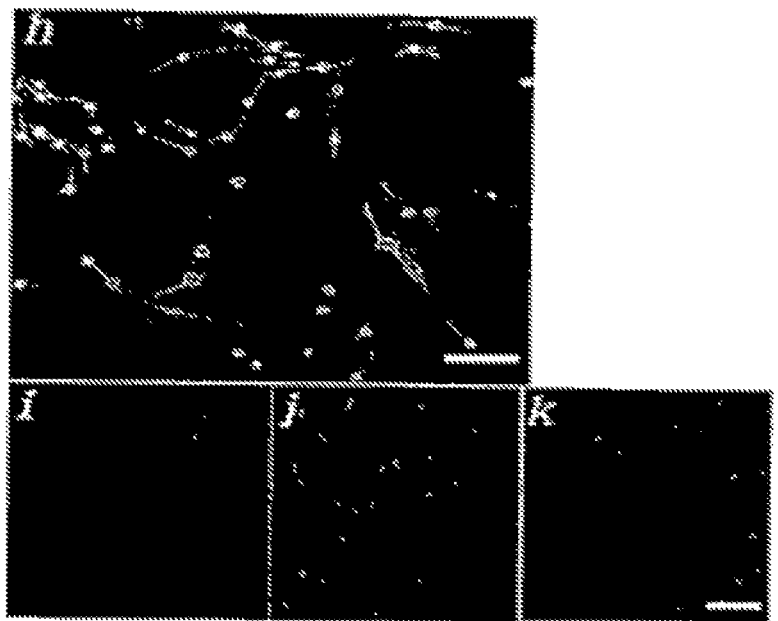
Fig.17i  Fig.17j  Fig.17k
Fig.17l
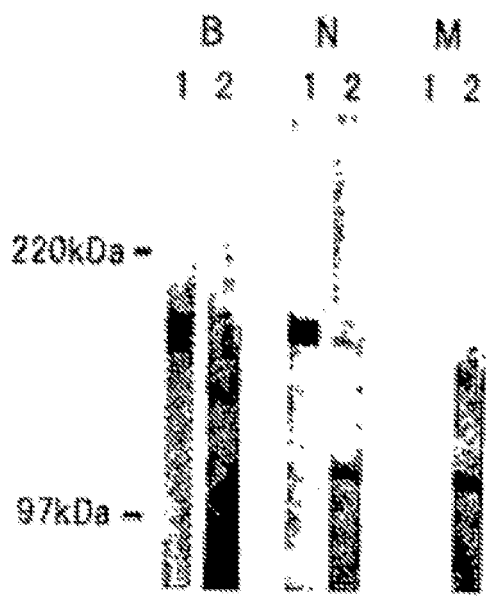
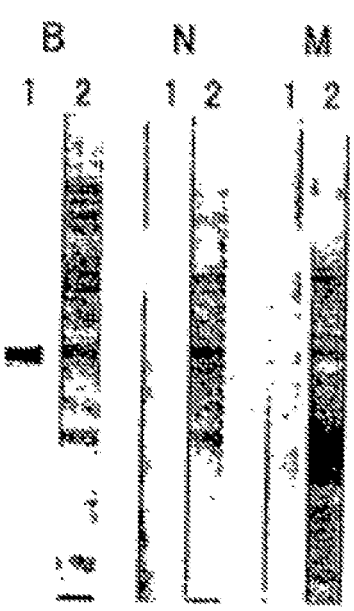

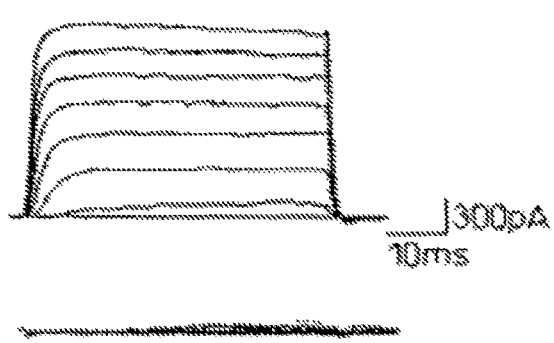
Fig.17m
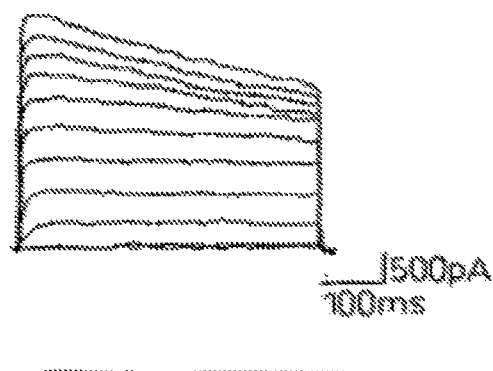
Fig.17n
Fig.17o
Fig.17p
Fig.17q

Fig.18
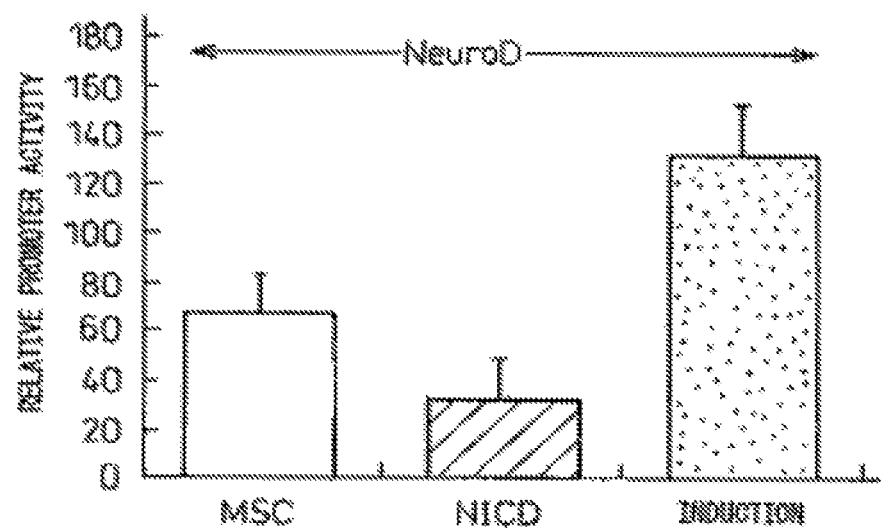
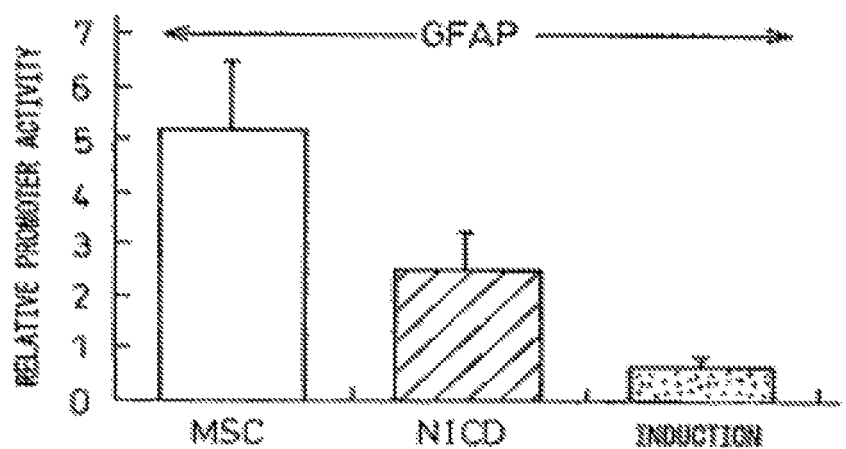

Fig.19b  Fig.19c
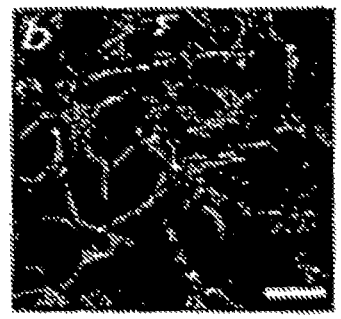
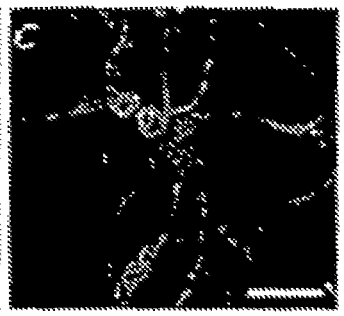
Fig.19d
Fig.19e
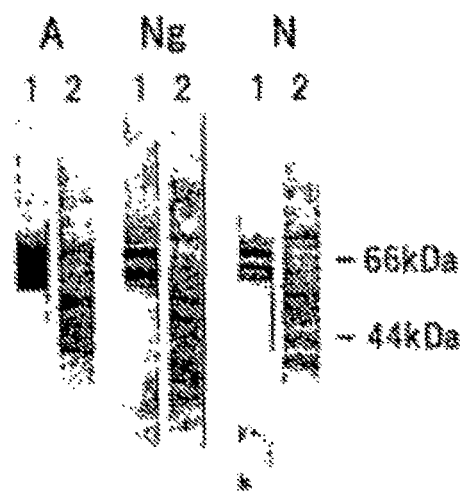

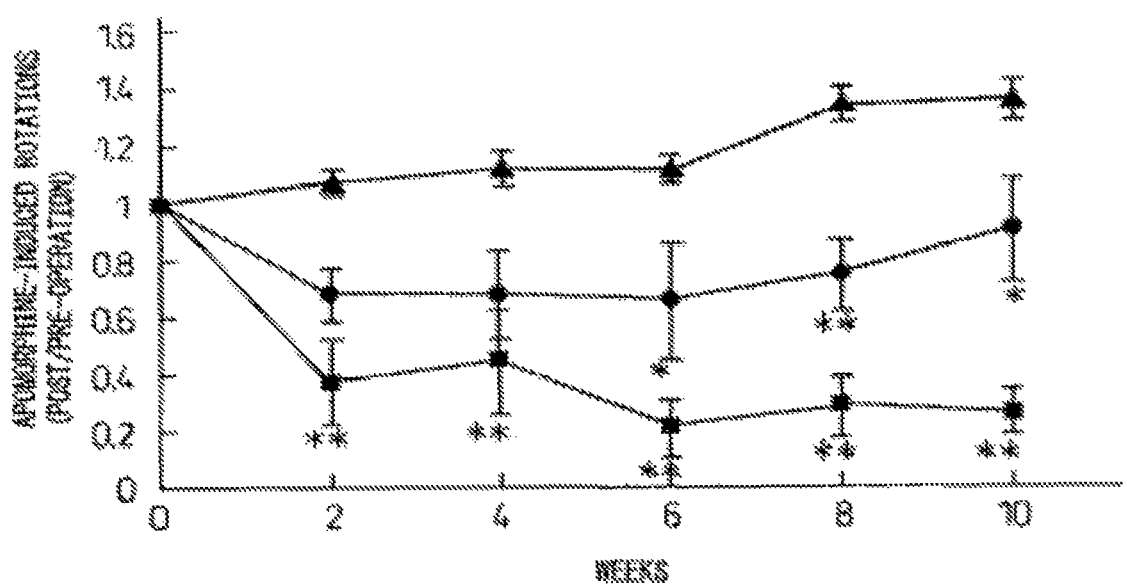

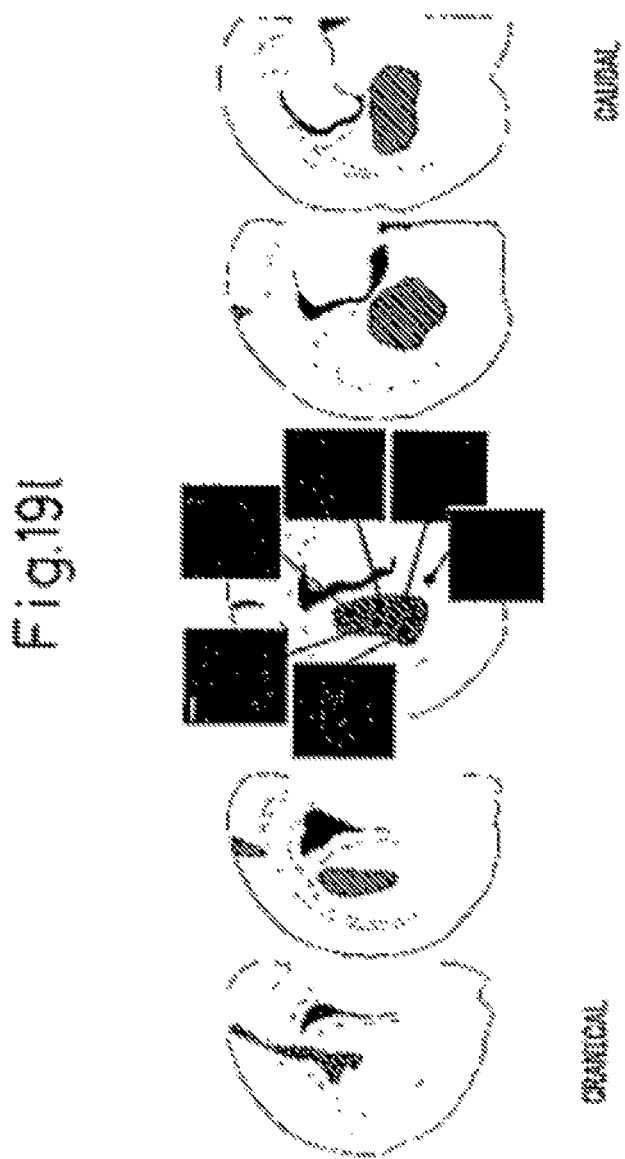

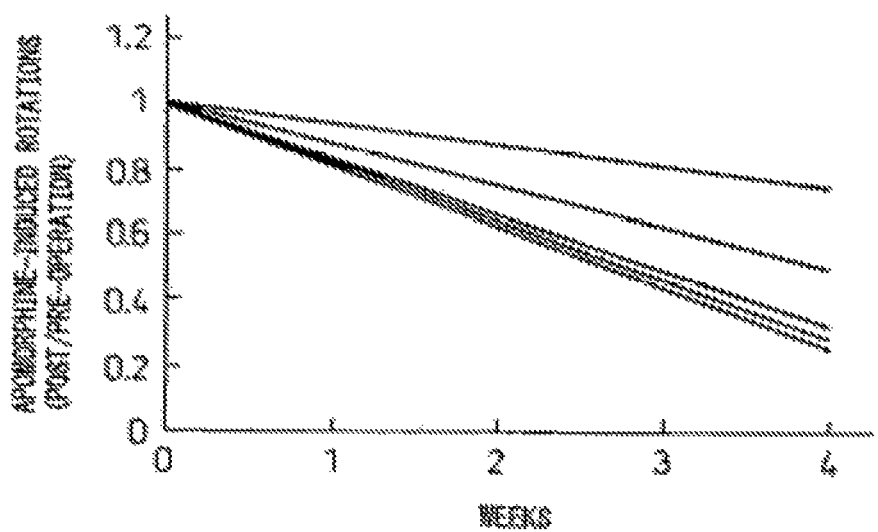

TREATMENT OF CNS DISORDERS USING DESCENDANTS OF MSCS EXPRESSING AN EXOGENOUS NOTCH INTRACELLULAR DOMAIN

CROSS-REFERENCE TO RELATED APPLICATIONS

This application is a continuation of U.S. patent application Ser. No. 13/733,510, filed on Jan. 3, 2013 (now U.S. Pat. No. 9,399,046 issued Jul. 26, 2016), which is a continuation of U.S. patent application Ser. No. 12/584,657 filed Sep. 10, 2009 (now U.S. Pat. No. 8,361,456 issued Jan. 29, 2013), which is a continuation of U.S. patent application Ser. No. 10/503,816 filed May 24, 2005 (now U.S. Pat. No. 7,682,825 issued Mar. 23, 2010), which is national phase under 35 U.S.C. 371 of International Patent Application Number PCT/JP2003/001260 filed Feb. 6, 2003, which claims priority to Japanese Patent Application Number 2002-030003 filed Feb. 6, 2002, the contents of which are incorporated herein by reference in its entirety their entireties.

TECHNICAL FIELD

The present invention relates to a method of inducing differentiation of bone marrow stromal cells to neural precursor cells or neural cells, and especially dopaminergic neurons, or to skeletal muscle cells by introduction of a Notch gene, and further relates to neural precursor cells, neural cells or skeletal muscle cells obtained by the method and to the therapeutic use of the cells and a treatment method.

BACKGROUND ART

Reconstruction of neural function in advanced neurodegenerative conditions such as Alzheimer's disease, Parkinson's disease, ALS (amyotrophic lateral sclerosis) and the like requires replacement of the neural cells lost by cell death. Although neural cell transplantation has been attempted in animal experiments using embryonic or adult neural stem cells, ES cells and embryonic neural cells, such uses face major hurdles against their application in humans. Ethical issues surround the use of embryonic stem cells or neural cells, and the question of guaranteeing a stable supply is also a concern. The demonstrated ability of ES cells to differentiate is currently attracting much attention, but in addition to the numerous ethical issues, the cost and labor required to induce differentiation to specific cell types and the risk of forming teratoid tumors after transplantation are factors impeding stable application of this technology. In order to use adult neural stem cells, they must be extracted by craniotomy since they are found in a very limited core section of the central nervous system, and thus patients undergoing regenerative treatment are also exposed to a tremendous risk and burden.

Although approximately 10 years have passed since isolation of central nervous system stem cells in vitro, it has not yet been possible by the currently accepted protocols to differentiate neural stem cells and obtain large amounts of functional dopaminergic or cholinergic neurons (Lorenz Studer, Nature Biotechnology December issue, p. 117 (2001).

A research group led by Professors Samuel Weiss of Calgary University (Canada) and Tetsuro Shingo has achieved success in efficiently inducing differentiation of dopamine-producing neural cells by administering a mixture of several tyrosine hydroxylase inducing factors (TH cocktail) into mice brains, but no previous example exists of inducing differentiation of dopaminergic neurons and cholinergic neurons from bone marrow stromal cells as according to the present invention.

Motor neurons are acetylcholinergic, and their application to such intractable diseases as ALS (amyotrophic lateral sclerosis) has been considered. In ALS, death of spinal marrow motor neurons for reasons as yet unknown leads to loss of muscle controlling nerves, thereby preventing movement of muscles throughout the body including the respiratory muscles, and leading to death of the patient within 2-3 years after onset. Currently, no effective treatment exists for this condition, but rat ALS models are being established.

Most degenerative muscular diseases such as muscular dystrophy are progressive, and therefore transplantation of skeletal muscle cells may constitute an effective treatment. In healthy individuals, satellite cells present in muscle tissue supplement for skeletal muscle that has lost its regenerative capacity, but in progressive muscular diseases the number of such cells is reduced and regenerative capacity is accordingly lower. Thus, while transplantation of skeletal muscle or its precursor cells can be used as treatment, no effective curative means yet exists.

In the course of development of the central nervous system, neurons and glial cells are induced to differentiate from relatively homogeneous neural precursor cells or neural stem cells. A mechanism is in place whereby some of the cells in the precursor cell population differentiate to certain cell subtypes in response to differentiation signals, while the other cells remain undifferentiated. Specifically, previously differentiated cells send out certain signals to their surrounding cells to prevent further differentiation to cells of their own type. This mechanism is known as lateral inhibition. In *Drosophila*, cells already differentiated to neurons express the "Delta" ligand while their surrounding cells express the Delta receptor "Notch", and binding of the ligand with receptor ensures that the surrounding cells do not differentiate to neural cells (Notch signaling). The Delta-Notch system appears to function in spinal cord cells as well (see, for example, Chitnis A., Henrique, D., Lewis, J., Ish-Horowicz, D., Kintner, C.: Nature, 375, 761-766(1995)).

It is thought that cellular interaction via the membrane protein Notch plays a major role in the development process whereby a homogeneous cell group produces many diverse types, and specifically, that upon ligand stimulation by adjacent cells, Notch induces expression of HES1 or HES5 which inhibit bHLH (basic helix-loop-helix) neurodifferentiation factors such as Mash1, Math1 and neurogenin, to suppress differentiation to the same cell type as the adjacent cell (see, for example, Kageyama et al., Saibo Kogaku [Cell Engineering] Vol. 18, No. 9, 1301-1306(1999)).

The Notch intracellular pathway is currently understood as follows. When Notch is first activated by ligands on the surface of adjacent cells (Delta, Serrate, Jagged), its intracellular domain is cleaved off (Artavanis-Tsakonas S. et al.: Science (1999)284:770-776 and Kageyama et al., Saibo Kogaku [Cell Engineering] Vol. 18, No. 9, 1301-1306 (1999)). After cleavage of the intracellular domain of Notch, it migrates from the cell membrane to the nucleus with the help of a nuclear localization signal (NLS) and in the nucleus forms a complex with the DNA-binding protein RBP-JK (Honjo T.: Genes Cells (1996) 1:1-9 and Kageyama et al., Saibo Kogaku [Cell Engineering] Vol. 18, No. 9, 1301-1306(1999)). RBP-JK itself is a DNA-binding repressor of transcription, and in the absence of activated Notch it binds to the promoter of the HES 1 gene, which is a differentiation inhibiting factor, thereby blocking its expression; however, once the complex forms between RBP-JK and the intracellular domain of Notch, the complex acts instead to activate transcription of the HES1 gene (see Jarriault S. et al.: Nature (1995) 377:355-358, Kageyama R. et al.: Curr. Opin. Genet. Dev. (1997) 7:659-665 and Kageyama et al., Saibo Kogaku [Cell Engineering] Vol. 18, No. 9, 1301-1306(1999)). This results in expression of HES1 and HES1-induced suppression of differentiation. In other words, Notch is believed to suppress differentiation via HES1 (see Kageyama et al., Saibo Kogaku [Cell Engineering] Vol. 18, No. 9, 1301-1306(1999)).

In mammals as well, it has become clear that Notch-mediated regulation of gene expression is important in maintaining neural precursor cells or neural stem cells and in the highly diverse process of neural differentiation, and that the Notch pathway is also essential for differentiation of cells other than those of the nervous system (see Tomita K. et al.: Genes Dev. (1999) 13:1203-1210 and Kageyama et al., Saibo Kogaku [Cell Engineering] Vol. 18, No. 9, 1301-1306(1999)). In addition, the existence of a HES independent Notch pathway, negative regulation of Notch signaling on the transcription level and negative interaction on the protein levd have also been anticipated (see Goh, M., Saibo Kogaku [Cell Engineering] Vol. 18, No. 9, 1291-1300 (1999)). Still, all of the aforementioned publications either teach or suggest that Notch signaling acts in a direction which suppresses differentiation.

Central nervous disorders in which reconstruction is not an option actually include a variety of different conditions with a high incidence rate in the population, from injury-induced spinal damage or cerebrovascular impairment or glaucoma which leads to blindness, to neurodegenerative conditions such as Parkinson's disease. Research on neuroregenerative methods to treat such diseases is therefore an urgent social need, and the results of this research by the present inventors is believed to be a breakthrough for application to humans. Bone marrow stromal cells are easily extracted by bone marrow aspiration on an outpatient basis, and due to their highly proliferative nature they can be cultured in large amounts within a relatively short period. Moreover a tremendous advantage may be expected since autologous transplantation can be carried out if nerves are formed from one's own bone marrow stem cells. The lack of immunological rejection would dispense with the need for administering immunosuppressants, thus making safer treatment possible. Furthermore, since bone marrow stem cells can be obtained from a bone marrow bank, this method is realistically possible from a supply standpoint. If such cells can be used to derive neural cells, for which no effective means has heretofore existed, then a major effect may be expected in the field of regenerative medicine.

ALS (amyotrophic lateral sclerosis) is a condition in which cell death of spinal marrow motor neurons for reasons as yet unknown leads to loss of muscle controlling nerves, thereby preventing movement of muscles throughout the body including the respiratory muscles and leading to death of the patient within 2-3 years after onset, but at the current time no effective treatment exists. Formation of acetylcholinergic neurons from one's own bone marrow stem cells would allow autologous transplantation, and this would offer a major benefit that might even serve as a cure for ALS.

Effective treatment methods also currently do not exist for muscular diseases such as muscular dystrophy, a degenerative disease of the skeletal muscle. A major benefit would also be afforded for such conditions, since formation of skeletal muscle cells from one's own bone marrow stem cells would allow autologous transplantation. Using such cells to derive skeletal muscle cells, for which no effective means has heretofore existed, would also be expected to provide a major effect in the field of regenerative medicine.

The possible applications of this technology are not only in the field of clinical treatment but also in the area of engineering of artificial organs and the like, which is expected to be an important field of development in the future. If neural cells or muscle cells could be easily produced on a cell culturing level, then applications may be imagined for creation of hybrid artificial organs and the like.

BRIEF DESCRIPTION OF THE INVENTION

The present invention provides a method of inducing differentiation of bone marrow stromal cells to neural cells or skeletal muscle cells in vitro, which method comprises introducing a Notch gene and/or a Notch signaling related gene into the cells, wherein the finally obtained differentiated cells are the result of cell division of the bone marrow stromal cells into which the Notch gene and/or Notch signaling related gene have been introduced. The invention further provides a novel treatment method for neurodegenerative and skeletal muscle degenerative diseases which employs neural precursor cells, neural cells or skeletal muscle cells obtained by the aforementioned method.

BRIEF DESCRIPTION OF THE DRAWINGS

FIGS. 14a to 14f show the features of isolated bone marrow stromal cells (MSC). FIG. 14a shows FACS analysis results for rat (MSC). The cells expressed CD29 (β1-integrin), CD90 (Thy-1) and CD54 (ICAM), but not CD34 (hemopoietic stem cell marker) or CD11b/c (macrophage-related marker). FIGS. 14b and 14c are phase contrast micrographs of non-treated rat MSCs (b) and non-treated human MSCs (c). FIGS. 14d to 14f are immunohistochemical photographs of CD29 (d), CD90 (e) and CD34 (f) in human MSCs. The MSCs were positive for CD29 and CD90, but negative for CD34. The bar represents 50 μm.

FIGS. 15a to 15h show phenotypes after NICD (Notch intracellular domain) transfection. FIG. 15a shows the results of RT-PCR for the Notch extracellular domain (ECD) and intracellular domain (ICD) in rat MSC, before NICD transfection (lane 1) and after NICD transfection (lane 2). Since ECD was detected in the non-treated MSC, a small amount of endogenous Notch was naturally expressed. After NICD transfection, however, ECD was down-regulated and NICD slightly up-regulated. FIGS. 15b to 15g are immunohistochemical photographs for GLAST (b, c), 3-PGDH (d, e) and nestin (f, g) in non-treated rat MS Cs (b, d, f) and NICD-transfected rat MS Cs (c, e, g). The bar represents 50 μm in b, c, d and g and 80 μm in e and f FIG. 15h is a graph showing 3-PGDH promoter activity for non-treated rat MSCs (MSC) and NICD-transfected rat MSCs (NICD). Both the full-length form of 3-PGDH and the truncated form (M1965) showed 9- to 10-fold increases in promoter activity after NICD transfection (p<0.01).

FIGS. 17a to 17q show the analysis results for induced neural cells. FIGS. 17a to 17c are phase contrast micrographs of neural cells induced from rat MSCs (a, b) and human MSCs (c). The bar represents 200 μm in FIG. 17a and 50 μm in FIGS. 17b and 17c. FIGS. 17d to 17g and 17i to 17k are immunohistochemical photographs of neuron matters and glia markers in rat MSCs (f, g, i, j, k) and human MSCs (d, e) (5 days) after introduction of trophic factors. The markers MAP-2ab (d) and neurofilament-M (e) were detected in human MSC, while β3-tubulin (f) and TuJ-1 (g) were expressed in rat MSCs. None of the rat or human cells reacted with the glia markers GF AP (i), GalC G) and 04 (k). The bar represents 100 μm in d, e and f, 60 μm in g and 100 μm in i to k. FIG. 17h shows Brd-U labeling of neural cells. MAP-2ab positive cells (Alexa Fluor 488-labeled, green code) did not incorporate Brd-U (Alexa Fluor 546-labeled, red code). FIG. 17l shows Western blot analysis results for the MAP-2ab rat sample (1) and GF AP rat sample (2). Lane 1 is Western blotting and lane 2 is a ponceau S stain. The non-treated MSCs (M) expressed neither MAP-2ab nor GF AP. On the 5th day (N) after introducing the trophic factors, the MSCs were MAP-2ab positive but were still negative for GFAP. Brain (B) was used as a positive control for both MAP-2ab and GFAP. FIGS. 17m to 17q show the results of a patch clamp test with neural cells induced from rat MSCs (m) and neural cells induced from human MSCs (n, p). Induction resulted in a dramatic increase in rectified K+ current up to approximately 1600 pA and 3000 pA in the rat MSCs (m) and human MSCs (n), respectively, compared to the non-treated MSCs (o, p). FIG. 17q shows a phase contrast micrograph of human MS Cs recorded in FIG. 17n.

FIG. 18 is a pair of graphs showing relative promoter activities of Neuro D and GF AP for non-treated rat MSCs (MSC), NICD-transfected rat MSCs (NICD) and neural-induced rat MSCs (induced).

FIGS. 19a to 19m show the results of transplantation into rat Parkinson's disease models. FIG. 19a is a graph showing the percentages of the following neurotransmitters in rat MSCs after trophic factor induction: y-aminobutyric acid (GABA); 0.3±0.1, vasoactive intestinal peptide (VIP); 0.5±0.1, serotonin (Ser); 2.0±0.4, glutamate (Glu); 2.3±0.7, substance P (SP); 2.4±0.9, TH; 3.9±0.6, vesicular acetylcholine transporter (V ACht); 5.2±2.4, calcitonin gene related peptide (CGRP); 5.3±0.8, neuropeptide Y (NPY) 6.1±1.6. With subsequent administration of GDNF, the percentage of TH-positive cells increased drastically to 41.0±14.1 (G-TH). FIGS. 19b and 19c show TH expression in human MSCs after trophic factor induction and then after GDNF treatment. The human MSCs exhibited the same response as rat MSCs, with TH-positive cells clearly increasing after GDNF treatment. The bar represents 100 μm in band 30 μm in c. FIG. 19d shows the results or RT-PCR of Nurr-1 in rat MSCs. Increased Nurr-1 up-regulation was observed after administration of GDNF (Ng) compared to the cells after trophic factor introduction alone (N). FIG. 19e shows a Western blot for TH in rat MSCs. TH expression was weak in MSCs after trophic factor induction (N), but increased after GDNF induction (Ng). Adrenal medulla (A) served as a positive control. Lane 1 is Western blotting and lane 2 is a ponceau S stain. FIG. 19f is a graph showing behavioral effects after grafting rat MS Cs into the striatum. The graph shows apomorphine-induced rotation in an MSC group (▲-▲), NMSC group (•-•) and G-MSC group (■-■) (*: 0.01<p<0.05; : p<0.01). FIGS. 19g to 19k are immunostaining photographs for neurofilament-M (g), TH (h), DAT (i), GF AP G) and 04 (i) in striatum at the 10th week after transplantation into the G-MSC group. Signals for these markers were all labeled with Alexa 546. The grafted rat MSCs were first labeled with GFP. Doubling of GFP-neurofilament, GFP-TH and GFP-DAT was observed in g, h and i, but not with GF AP staining or 04 staining. The bar represents 50 μm. FIG. 19l** is a set of sectional illustrations showing integration of GFP-labeled rat MSCs (G-MSC group) into the striatum. Confocal images after immunohistochemistry for TH are indicated from regions marked by dots in the diagram. The bar represents 50 µm. FIG. 19m is a graph showing apomorphine induced rotation in rats after transplantation of GDNF-treated human neural MSCs. The results from 5 rats (mean rotation: 0.44±0.2) are shown up to four weeks after grafting (with one rat represented by each line). MSCs after trophic factor induction: y-aminobutyric acid (GABA); 0.3±0.1, vasoactive intestinal peptide (VIP); 0.5±0.1, serotonin (Ser); 2.0±0.4, glutamate (Glu); 2.3±0.7, substance P (SP); 2.4±0.9, TH; 3.9±0.6, vesicular acetylcholine transporter (V ACht); 5.2±2.4, calcitonin gene related peptide (CGRP); 5.3±0.8, neuropeptide Y (NPY) 6.1±1.6. With subsequent administration of GDNF, the percentage of TH-positive cells increased drastically to 41.0±14.1 (G-TH). FIGS. 19b and 19c show TH expression in human MSCs after trophic factor induction and then after GDNF treatment. The human MSCs exhibited the same response as rat MSCs, with TH-positive cells clearly increasing after GDNF treatment. The bar represents 100 µm in band 30 µm in c. FIG. 19d shows the results or RT-PCR of Nurr-1 in rat MSCs. Increased Nurr-1 up-regulation was observed after administration of GDNF (Ng) compared to the cells after trophic factor introduction alone (N), FIG. 19e shows a Western blot for TH in rat MSCs. TH expression was weak in MSCs after trophic factor induction (N), but increased after GDNF induction (Ng). Adrenal medulla (A) served as a positive control. Lane 1 is Western blotting and lane 2 is a ponceau S stain. FIG. 19f is a graph showing behavioral effects after grafting rat MS Cs into the striatum. The graph shows apomorphine-induced rotation in an MSC group (▲-▲), NMSC group (●-●) and G-MSC group (■-■)(*: $0.01<p<0.05$; **; $p<0.01$). FIGS. 19g to 19k are immunostaining photographs for neurofilament-M (g), TH (h), DAT (i), GE AP G) and 04 (i) in striatum at the 10th week after transplantation into the G-MSC group. Signals for these markers were all labeled with Alexa 546. The grafted rat MSCs were first labeled with GFP. Doubling of GFP-neurofilament. GFP-TH and (GFP-DAT was observed in g, h and i, but not with GF AP staining or 04 staining. The bar represents 50 µm, FIG. 19l is a

DETAILED DESCRIPTION OF THE INVENTION

Figure 1:
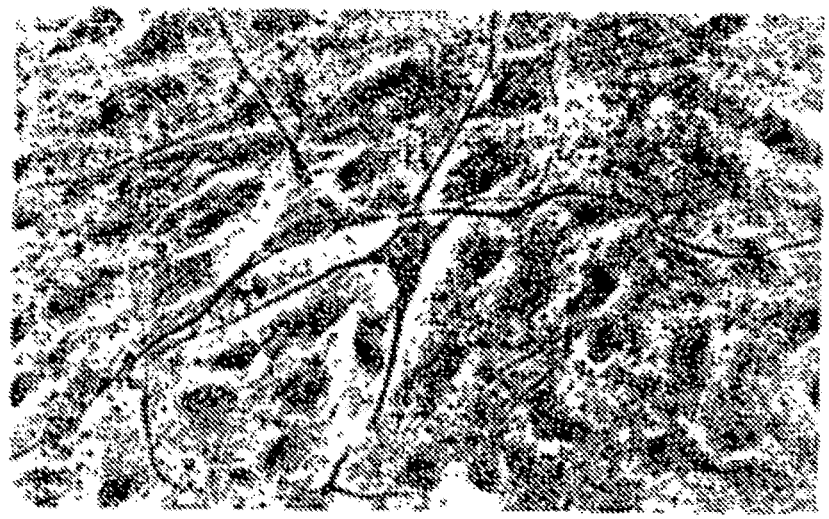
FIG. 1 is a micrograph (phase contrast microscope) in lieu of a drawing, showing neural cells induced to differentiate according to the invention.

The present inventors investigated stimulation of bone marrow stromal cells by introduction of genes which play a central role in the initial stages of morphogenesis of bone marrow stromal cells, and examined the effects of such stimulation on induction of bone marrow stromal cell differentiation. Specifically, it was expected to be potentially possible to "reset" bone marrow stromal cells by introduction of Notch genes and Notch signaling genes, which play important roles in developmental differentiation of the nervous system and perform functions in determining cell fates when precursor cells branch to neural cells or glial cells.

It is important to note that despite implication of Notch genes and Notch signaling related genes in the mechanism of suppressing induction of cell differentiation, it was a completely unexpected finding that combining introduction of Notch genes and Notch signaling related genes with other stimulation to induce differentiation, can also induce differentiation of the very cells into which the Notch genes and Notch signaling related genes have been introduced (not the cells contacting with the cells into which the Notch genes and Notch signaling related genes have been introduced). It cannot be affirmed that introduction of the Notch genes and Notch signaling related genes in the differentiation inducing method of the present invention resulted in resetting of developmental differentiation of bone marrow stromal cells. However, by combination of this gene introduction with other differentiation inducing steps according to the invention, it was possible as a result to provide a method of efficiently inducing differentiation of bone marrow stromal cells to neural cells or skeletal muscle cells.

As a result of repeated experimentation in combining steps comprising introduction of Notch genes and Notch signaling related genes, the present inventors have been the first to succeed in efficiently inducing differentiation of bone marrow stromal cells to neural cells or skeletal muscle cells in vitro. Moreover, it was confirmed that upon grafting of the neural cells obtained by the differentiation inducing method into rat Parkinson's disease models or rat optic nerve damage-associated retinal or optic nerve degeneration models, the grafted nerves actually took and functioned, and the present invention was thus completed.

Surprisingly, by introducing Notch genes and Notch signaling related genes into bone marrow stromal cells, by administration of various factors and cytokines believed to be involved in promoting neural differentiation, and by increasing intracellular cAMP which is considered to be a general trigger for initiation of differentiation, it was possible to successfully induce differentiation of bone marrow stromal cells to neural cells under in vitro culturing conditions. We confirmed not only expression of MAP-2 and neurofilament which are specific to neural cells, but also expression of the neurotransmitter synthetase tyrosine hydroxylase and production of neurotransmitters such as acetylcholine, neuropeptide Y and substance P.

On the other hand, it has been suggested that demethylation and activation of one or a very few genes by 5-azacytidine (5-AZC) leads to conversion to myoblasts (see Taylar S M, Jones P A: Cell 17:771-779, 1979 and Nabeshima Y., Seitai no Kagaku 47(3):184-189, 1996). We therefore combined the aforementioned introduction of Notch genes and Notch signaling related genes into neural cells with the aforementioned demethylation by treatment with 5-azacytidine (5-AZC). Specifically, by eliminating suppressed expression by methylation of the genes using the aforementioned demethylating agent to reset bone marrow stromal cells, subsequently introducing the Notch and Notch signaling related genes and co-culturing the gene-introduced cells together with bone marrow stromal cells without the genes, and finally treating the cells with an augmenting agent for intracellular cAMP which is considered to be a general trigger for initiating differentiation, we succeeded in inducing differentiation of the Notch and Notch signaling related gene-introduced cells to skeletal cells by culturing in vitro. Characteristic polynucleated myotube formation and striation were found in the resultant cells, and expression of the muscle-specific proteins myogenin and Myf5 was also confirmed on the mRNA level.

According to one mode of the invention, there is provided a method of inducing differentiation of bone marrow stromal cells to neural cells or skeletal muscle cells in vitro, which method comprises introducing a Notch gene and/or a Notch signaling related gene into the cells, wherein the resultant differentiated cells are the offspring of cell division of the bone marrow stromal cells into which the Notch gene and/or Notch signaling related gene have been introduced.

According to another mode of the invention, there is provided a method of inducing bone marrow stromal cells to differentiate into neural precursor cells in vitro comprising the steps of:

(1) isolating bone marrow stromal cells from bone marrow, and culturing the cells in a standard essential culture medium supplemented with a serum; and (2) introducing a Notch gene and/or a Notch signaling related gene into the cells, and further culturing the calls to produce neural precursor cells.

The isolated bone marrow stromal cells may be human cells.

According to yet another mode of the invention, there are provided neural precursor cells produced by the aforementioned method.

According to yet another mode of the invention, there are provided neural precursor cells which express the neural precursor cell markers GLAST, 3PGDH and nestin.

According to yet another mode of the invention, there is provided a method of inducing bone marrow stromal cells to differentiate into neural cells in vitro comprising the steps of:

(1) isolating bone marrow stromal cells from bone marrow, and culturing the cells in a standard essential culture medium supplemented with a serum;

(2) introducing a Notch gene and/or a Notch signaling related gene into the cells, and further culturing the calls; and (3) adding a cyclic AMP-augmenting agent or a cyclic AMP analogue, and/or a cell differentiation stimulating factor to the culture medium, and further culturing the cells to produce the neural cells, wherein the resultant differentiated cells are offspring of cell division of the bone marrow stromal cells into which the Notch gene and/or Notch signaling related gene have been introduced.

The standard essential culture medium may be an Eagle's alpha modified minimum essential medium, and the serum may be fetal bovine serum.

The introduction of the Notch gene and/or Notch signaling related gene may be accomplished by lipofection with a mammalian expression vector.

The method may also comprise, between steps (2) and (3), a step of selecting cells into which the genes have been introduced, for a predetermined period of time.

The cyclic AMP-augmenting agent or cyclic AMP analogue may be forskolin, and its concentration may be 0.001 nM to 100 μM.

The cell differentiation stimulating factor may be selected from the group consisting of basic fibroblast growth factor (bFGF), ciliary neurotrophic factor (CNTF) and mixtures thereof.

The concentration of the cell differentiation stimulating factor may be between 0.001 ng/ml and 100 μg/ml.

The isolated bone marrow stromal cells are preferably human cells.

According to yet another mode of the invention, there are provided neural cells produced by the aforementioned method.

According, to yet another mode of the invention, there are provided neural cells which express the neural cell markers β-tubulin isotype 3 and TuJ-1.

According to yet another mode of the invention, there is provided a method of inducing bone marrow stromal cells to differentiate into dopaminergic neurons in vitro comprising the steps of:

(1) isolating bone marrow stromal cells from bone marrow, and culturing the cells in a standard essential culture medium supplemented with a serum;

(2) introducing a Notch gene and/or a Notch signaling related gene into the cells, and further culturing the cells;

(3) adding a cyclic AMP-augmenting agent or a cyclic AMP analogue, and/or a cell differentiation stimulating factor to the culture medium, and further culturing the cells to produce the neural cells;

(4) culturing the neural cells obtained in Step (3) in a standard essential culture medium supplemented with a serum; and (5) adding glial derived neurotrophic factor (GDNF), and a cyclic AMP-augmenting agent or a cyclic AMP analogue, and/or a cell differentiation stimulating factor other than glial derived neurotrophic factor to the culture medium, and further culturing the cells to obtain dopaminergic neurons, wherein the resultant dopaminergic neurons are offspring of bone marrow stromal cells into which the Notch gene and/or Notch signaling related gene have been introduced.

The standard essential culture medium in Step (4) may be an Eagle's alpha modified minimum essential medium.

The serum in Step (4) may be fetal bovine serum.

The cyclic AMP-augmenting agent or cyclic AMP analogue in Step (5) may be forskolin. The concentration of the cyclic AMP-augmenting agent or cyclic AMP analogue in Step (5) may be between 0.001 nM and 100 μM.

The cell differentiation stimulating factor other than glial derived neurotrophic factor in Step (5) may be selected from the group consisting of basic fibroblast growth factor (bFG), platelet-derived growth factor-AA (PDGF-AA) and mixtures thereof.

The concentration of glial derived neurotrophic factor in (Step 5) may be between 0.001 ng/ml and 100 μg/ml, and is preferably between 1 ng/ml and 100 ng/ml.

The concentration of the cell differentiation stimulating factor other than glial derived neurotrophic factor in Step (5) may be between 0.001 ng/ml and 100 μg/ml.

The isolated bone marrow stromal cells are preferably human cells.

According to yet another mode of the invention, there are provided dopaminergic neurons produced by the aforementioned method.

According to yet another mode of the invention, there is provided a method of inducing bone marrow stromal cells to differentiate into acetylcholinergic neurons in vitro comprising the steps of:

(1) isolating bone marrow stromal cells from bone marrow, and culturing the cells in a standard essential culture medium supplemented with a serum;

(2) introducing a Notch gene and/or a Notch signaling related gene into the cells, and further culturing the cells;

(3) adding a cyclic AMP-augmenting agent or a cyclic AMP analogue, and/or a cell differentiation stimulating factor to the culture medium, and further culturing the cells to produce the neural cells;

(4) culturing the neural cells obtained in Step (3) in a standard essential culture medium supplemented with a serum; and (5) adding nerve growth factor (NGF), and a cyclic. AMP-augmenting agent or a cyclic AMP analogue, and/or a cell differentiation stimulating factor other than nerve growth factor to the culture medium, and further culturing the cells to obtain acetylcholinergic neurons, wherein the resultant acetylcholinergic neurons are offspring of bone marrow stromal cells into which the Notch gene and/or Notch signaling related gene have been introduced.

The standard essential culture medium in Step (4) may be an Eagle's alpha modified minimum essential medium. The serum in Step (4) may be fetal bovine serum.

The cyclic AMP-augmenting agent or cyclic. AMP analogue in Step (5) may be forskolin. The concentration of the cyclic AMP-augmenting agent or cyclic AMP analogue in Step (5) may be between 0.001 nM and 100 µM.

The cell differentiation stimulating factor other than nerve growth factor in Step (5) may be selected from the group consisting, of basic fibroblast growth factor (bFG), platelet-derived growth factor-AA (PDGF-AA) and mixtures thereof.

The concentration of nerve growth factor in (Step 5) may be between 0.001 ng/ml and 100 µg/ml, and is preferably between 1 ng/ml and 100 ng/ml.

The concentration of the cell differentiation stimulating factor other than nerve growth factor in Step (5) may be between 0.001 ng/ml and 100 µg/ml.

The isolated bone marrow stromal cells are preferably human cells.

According to yet another mode of the invention, there are provided acetylcholinergic neurons produced by the aforementioned method.

According to yet another mode of the invention, there is provided a method of inducing bone marrow stromal cells to differentiate into skeletal muscle cells in vitro, comprising the steps of:

(1) isolating bone marrow stromal cells from bone marrow, and culturing the cells in a standard essential culture medium supplemented with a serum;

(2) adding a demethylating agent to the culture medium, and further culturing the cells;

(3) adding a cyclic AMP-augmenting agent or a cyclic AMP analogue, and/or a cell differentiation stimulating factor to the culture medium, and further culturing the cells;

(4) introducing a Notch gene and/or a Notch signaling related gene into the cells, and further culturing the cells;

(5) co-culturing the cells into which the genes have been introduced, with nontreated bone marrow stromal cells into which the genes have not been introduced; and (6) adding a cyclic AMP-augmenting agent or a cyclic AMP analogue to the culture medium, and further culturing the cells to obtain skeletal muscle cells, wherein the resultant differentiated cells are offspring of bone marrow stromal cells into which the Notch gene and/or Notch signaling related gene have been introduced.

The standard essential culture medium may be an Eagle's alpha modified minimum essential medium, and the serum may be fetal bovine serum.

The demethylating agent may be 5-azacytidine, and its concentration may be between 30 nmol/l and 300 µmol/l.

The cyclic AMP-augmenting agent or cyclic AMP analogue in Step (3) may be forskolin.

The concentration of the cyclic AMP-augmenting agent or cyclic AMP analogue in Step (3) may be between 0.001 nM and 100 µM.

The cell differentiation stimulating factor may be selected from the group consisting of basic fibroblast growth factor (bFGF), platelet-derived growth factor-AA (PDGF-AA), heregulin, and mixtures thereof, and its concentration may be between 0.001 ng/ml and 100 µg/ml. The introduction of the Notch gene and/or Notch signaling related gene may be accomplished by lipofection with a mammalian expression vector.

The method may also comprise, between steps (4) and (5), a step of selecting cells into which the genes have been introduced, for a predetermined period of time.

The cyclic AMP-augmenting agent or cyclic AMP analogue in Step (5) may be forskolin.

The concentration of the cyclic AMP-augmenting agent or cyclic AMP analogue in Step (5) may be between 0.001 nM and 100 µM.

The isolated bone marrow stromal cells are preferably human cells.

According to yet another mode of the invention, there are provided skeletal muscle cells produced by the aforementioned method.

According to yet another mode of the invention, there is provided a method for treatment of a patient suffering from a disease, disorder or condition of the central nervous system, which method comprises administering a therapeutically effective amount of the aforementioned neural precursor cells into the region of the central nervous system of the patient in which the disease, disorder or condition is found, wherein the presence of the neural precursor cells exerts a therapeutic effect on the disease, disorder or condition.

According to yet another mode of the invention, there is provided the use of a therapeutically effective amount of the aforementioned neural precursor cells in the manufacture of a pharmaceutical composition for treatment of a patient suffering from a disease, disorder or condition of the central nervous system.

According to yet another mode of the invention, there is provided a method for treatment of a patient suffering from a disease, disorder or condition of the central nervous system, which method comprises administering a therapeutically effective amount of the aforementioned neural cells into the region of the central nervous system of the patient in which the disease, disorder or condition is found, wherein the presence of the neural cells exerts a therapeutic effect on the disease, disorder or condition.

According, to yet another mode of the invention, there is provided the use of a therapeutically effective amount of the aforementioned neural cells in the manufacture of a pharmaceutical composition for treatment of a patient suffering from a disease, disorder or condition of the central nervous system.

According to yet another mode of the invention, there is provided a method for treatment of a patient suffering from a disease, disorder or condition of the central nervous system, which method comprises administering a therapeutically effective amount of the aforementioned neural cells which express the neural cell markers $\beta$-tubulin isotype 3 and TuJ-1 into the region of the central nervous system of the patient in which the disease, disorder or condition is found, wherein the presence of the neural cells exerts a therapeutic effect on the disease, disorder or condition.

According to yet another mode of the invention, there is provided the use of a therapeutically effective amount of the aforementioned neural cells which express the neural cell markers $\beta$-tubulin isotype 3 and TuJ-1 in the manufacture of a pharmaceutical composition for treatment of a patient suffering from a disease, disorder or condition of the central nervous system.

According to yet another mode of the invention, there is provided a method for treatment of a patient suffering from a disease, disorder or condition of the central nervous system, which method comprises administering a therapeutically effective amount of the aforementioned dopaminergic neurons into the region of the central nervous system of the patient in which the disease, disorder or condition is found, wherein the presence of the neural cells exerts a therapeutic effect on the disease, disorder or condition.

According to yet another mode of the invention, there is provided the use of a therapeutically effective amount of the aforementioned dopaminergic neurons in the manufacture of a pharmaceutical composition for treatment of a patient suffering from a disease, disorder or condition of the central nervous system.

According to yet another mode of the invention, the disease, disorder or condition may be Parkinson's disease.

According to yet another mode of the invention, there is provided a method for treatment of a patient suffering from a disease, disorder or condition of the central nervous system, which method comprises administering a therapeutically effective amount of the aforementioned acetylcholinergic neurons into the region of the central nervous system of the patient in which the disease, disorder or condition is found, wherein the presence of the neural cells exerts a therapeutic effect on the disease, disorder or condition.

According to yet another mode of the invention, there is provided the use of a therapeutically effective amount of the aforementioned acetylcholinergic neurons in the manufacture of a pharmaceutical composition for treatment of a patient suffering from a disease, disorder or condition of the central nervous system.

The disease, disorder or condition may be selected from the group consisting of ALS (amyotrophic lateral sclerosis) and Alzheimer's disease.

According to yet another mode of the invention, there is provided a method for treatment of a patient suffering from a disease, disorder or condition associated with muscle degeneration, which method comprises administering a therapeutically effective amount of the aforementioned skeletal muscle cells into the region of muscular degeneration of the patient, wherein the presence of the skeletal muscle cells exerts a therapeutic effect on the disease, disorder or condition.

According to yet another mode of the invention, there is provided the use of a therapeutically effective amount of the aforementioned skeletal muscle cells in the manufacture of a pharmaceutical composition for treatment of a patient suffering from a disease, disorder or condition associated with muscle degeneration.

The disease, disorder or condition may be muscular dystrophy.

Throughout the present specification, the term "bone marrow stromal cells" refers to cells in the bone marrow which are not of the hemopoietic system and are potentially able to differentiate to osteocytes, chondrocytes, adipocytes and the like. Bone marrow stromal cells are identified by positivity for CD29 (β1-integrin), CD90 (Thy-1) and CD54 (ICAM-1) and negativity for CD34 (hemopoietic stem cell marker) and CD11b/c (macrophage marker).

The term "efficiently" as used throughout the present specification with respect inducing differentiation means that the selected bone marrow stromal cells are finally converted to neural cells or skeletal muscle cells at a high rate by the differentiation inducing method of the invention. The efficiency of the differentiation inducing method of the invention is 50% or greater, preferably 75% or greater, more preferably 80% or greater, even more preferably 85% or greater, yet more preferably 90% or greater and most preferably 95% or greater.

The term "neural precursor cells" as used throughout the present specification refers to bone marrow stromal cells immediately after introduction of a Notch gene and/or Notch signaling related gene, and specifically they are the cells prior to introduction of trophic factors.

The term "neural cells" as used throughout the present specification refers to neurons, which are characterized morphologically by a cell body and two types of processes (dendrites and axons), and biochemically by reaction with antibodies for β-tubulin isotope 3 and TuJ-1.

Neural cells are characterized by secreting neurotransmitters, neurotransmitter synthetases or neurotransmitter-related proteins, for example, tyrosine hydroxylase (TH), vesicular acetylcholine transporter, neuropeptide Y and substance P (SP).

Tyrosine hydroxylase is a marker for doparninergic neurons, while vesicular acetylcholine transporter is a marker for acetylcholinergic neurons which are typically motor neurons.

The term "glial cells" as used throughout the present specification refers to astrocytes, oligodendrocytes, microglia and epithelial cells found between neurons and their processes in the central nerves.

Glial acidic protein (GF AP) is a marker for astrocytes, and 04 is a marker for oligodendrocytes.

The term "skeletal muscle cells" as used throughout the present specification refers to myofibers or muscle fibers, and they are the individual myocytes of the skeletal muscle. Morphologically they are characterized as giant long, thin polynucleated cells with myotube formation and striation, while biochemically they are characterized by expressing transcription regulating factors such as myogenin and Myf5.

The method of inducing differentiation of bone marrow strornal cells into neural cells or skeletal muscle cells according to the invention is novel in the aspect of comprising a step of introducing a Notch gene and/or Notch signaling related gene into the aforementioned cells. Another novel aspect is that this step may be combined with other differentiation inducing steps of the prior art in a prescribed order. The selection and optimum combination of such steps according to the invention constitute a highly significant novel discovery by the present inventors. Bone marrow stromal cells had already been known as mesenchyrnal stem cells or precursor cells capable of being induced to differentiate to osteoblasts vascular endothelial cells, skeletal muscle cells, adipocytes and smooth muscle cells, but it was not known whether bone marrow stromal cells could actually be differentiated to neural cells or skeletal muscle cells, and this goal had not yet been successfully achieved despite vigorous attempts. While not intending to be constrained by any particular theory, the present inventors conjecture that introduction of a Notch gene and/or Notch gene signaling related gene into the aforementioned cells results in resetting of the cells in terms of developmental differentiation, and aid in the function of other differentiation inducing treatments.

The present invention will now be explained in greater detail by the following examples, with the understanding that these examples do not limit the scope of the invention in any way.

EXAMPLES

Example 1: Neural Induction

Stromal cells were extracted from the bone marrow of adult rats (Wistar rats) and cultured. The medium used was Minimum Essential Medium Alpha Eagle Modification (M4526, Sigma Co.) containing 20% fetal bovine serum (14-501F, Lot #61-1012, Bio Whittaker Co.).

After subculturing to four generations, the gene for the Notch intracellular domain was introduced when the cells reached 80-90% confluence. A 3.1 kb EcoRI-XbaI fragment of the Notch intracellular domain was inserted at the EcoRI-XbaI multicloning site of pCI-neo mammal expression vector (#E1841) by Promega for recombination. A LipofectAMINE 2000 (11668-027, Gibco BRL) system was used for the introduction.

On the day following introduction, G418 sulfate (83-5027, Gibco BRL) was added to a concentration of 200 ng/ml and introduced cells were selected for 10 days.

After restoration of the cell population to 90% confluence, 5 μM of forskolin (344273, Calbiochem), 10 ng/ml of basic fibroblast growth factor (100-18B, Peprotech EC, Ltd.) and 50 ng/ml of ciliary neurotrophic factor (557-NT, R&D Systems) were added.

Figure 2:
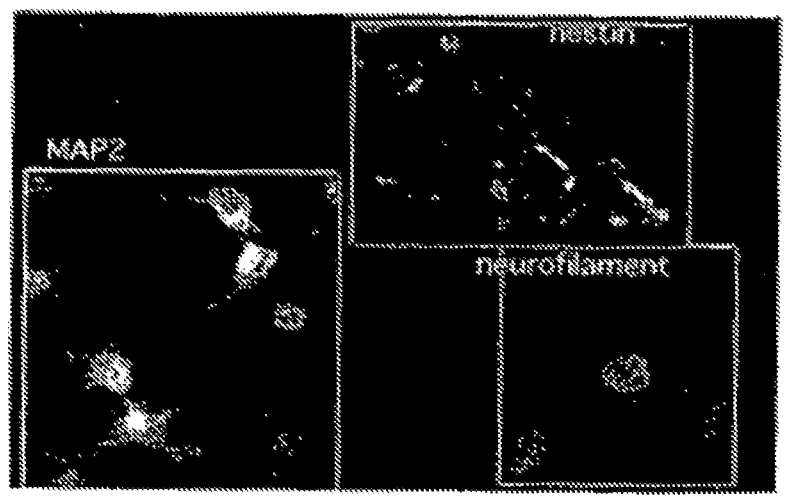
FIG. 2 is a composite of immunofluorescent photographs in lieu of a drawing, showing positive reactions of neural cells induced to differentiate according to the invention, against MAP-2 antibodies, neurofilament antibodies and nestin antibodies.

As a result of analyzing the cells after about 10 days, the characteristic morphology of neural cells was observed as shown in FIG. 1. The induced cells exhibited positive reaction for antibodies against MAP-2 (MAB364, Chemicon), neurofilament (814342, Boehringer Manheim) and nestin (BMS4353, Bioproducts), as shown in FIG. 2. Since MAP-2 and neurofilament are markers for neural cells and nestin is a marker for neural precursor cells, the induced cells were therefore judged to possess the properties of neural cells.

Figure 3:
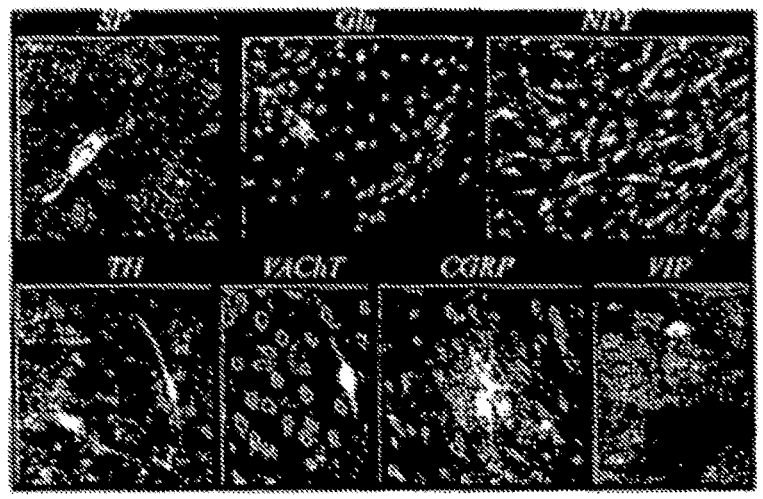
FIG. 3 is a composite of immunofluorescent photographs in lieu of a drawing, showing reactions of neural cells induced to differentiate according to the invention, against antibodies for the neurotransmitter synthetase tyrosine hydroxylase (TH) and the neurotransmitters or neurotransmitter-related peptides vesicular acetylcholine transporter (V AChT), neuropeptide V (NPY), substance P (SP), glutamine (Glu), calcitonin gene related peptide (CGRP) and vasoactive intestinal peptide (VIP).

A search conducted using antibodies against the neurotransmitter synthetase tyrosine hydroxylase (AB 151, Chemicon) and the neurotransmitters or eurotransmitter-related proteins vesicular acetylcholine transporter (AB1578, Chemicon), neuropeptide Y (RIN7172, Peninsula Lab Inc.), substance P (RPN1572, Amersham Inc.), etc., as shown in FIG. 3, revealed cells approximately 2-4% positive for each, thereby also indicating the presence of neurotransmitter-producing neural cells.

Figure 5:
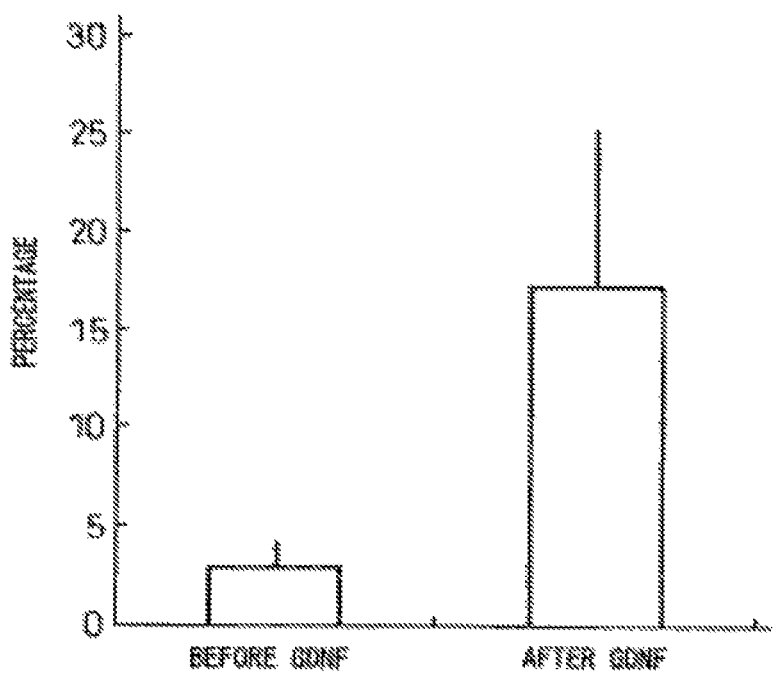
FIG. 5 is a graph showing changes in the tyrosine hydroxylase positivity (rate of dopaminergic neuron differentiation) of neural cells induced to differentiate according to the invention, before and after treatment with GDNF.

Neural cells were induced by this procedure, and at this stage 2.9±0.5% of the total differentiation-induced neural cells exhibited reaction for tyrosine hydroxylase, a marker for dopaminergic neurons, as shown at the left of the graph of FIG. 5. Also, as shown at the left of the graph in FIG. 7, 1.78±0.75% of the total differentiation-induced neural cells exhibited reaction for vesicular acetylcholine transporter, a marker for acetylcholinergic neurons which are typically motor neurons.

Example 2: Induction of Dopaminergic Neurons

The differentiation-induced neural cells were then cultured in Minimum Essential Medium Alpha Eagle Modification (M4526, Sigma Co.) containing 10% fetal bovine serum (14-501F, Lot #61-1012, Bio Whittaker Co.), with further addition of 50 ng/ml of glial derived neurotrophic factor (GDNF) (human recombinant GDNF, #450-10, Peprotech EC Ltd.), 5 μM of forskolin (344273, Calbiochem), 10 ng/ml of basic fibroblast growth factor (100-18B, Peprotech EC, Ltd.) and 5 ng/ml of platelet-derived growth factor-AA (396-HB, Peprotech EC Ltd.).

Figure 4:
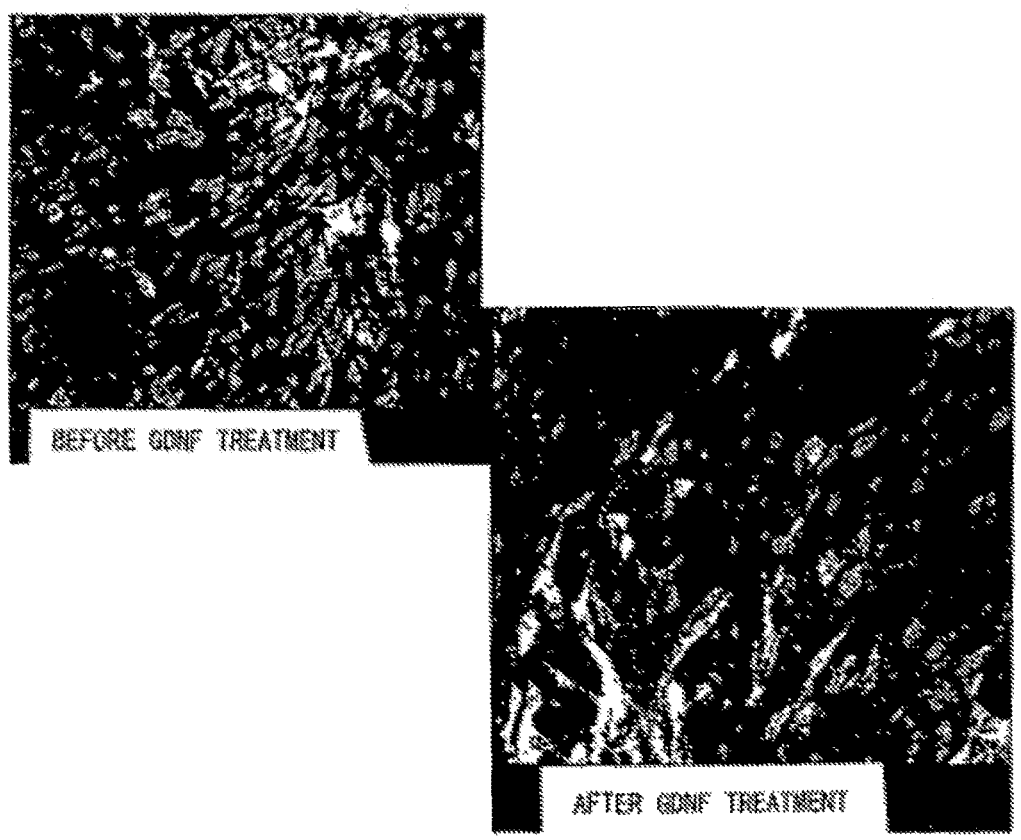
FIG. 4 is a pair of immunofluorescent photographs in lieu of a drawing, showing changes in the tyrosine hydroxylase positivity (rate of dopaminergic neuron differentiation) of neural cells induced to differentiate according to the invention, before and after treatment with GDNF.

As a result of this procedure, the dopaminergic neurons exhibiting reaction for tyrosine hydroxylase increased dramatically to 17.2±5.1 of the total neural cells (see right of graph in FIG. 5). As shown in the photograph of FIG. 4, the proportion of tyrosine hydroxylase protein stained green with FIPC increased dramatically after GDNF treatment.

Example 3: Induction of Acetylcholinergic Neurons

The differentiation-induced neural cells of Example 1 were cultured in Minimum Essential Medium Alpha Eagle Modification (M4526, Sigma Co.) containing 10% fetal bovine serum (14-501F, Lot #61-1012, Bio Whittaker Co.), with further addition of nerve growth factor (2.5 S NGF, #T002A, Takara), 5 μM of forskolin (344273, Calbiochem), 10 ng/ml of basic fibroblast growth factor (100-18B, Peprotech EC, Ltd.) and 5 ng/ml of platelet-derived growth factor-AA (396-HB, Peprotech EC Ltd.).

Figure 6:
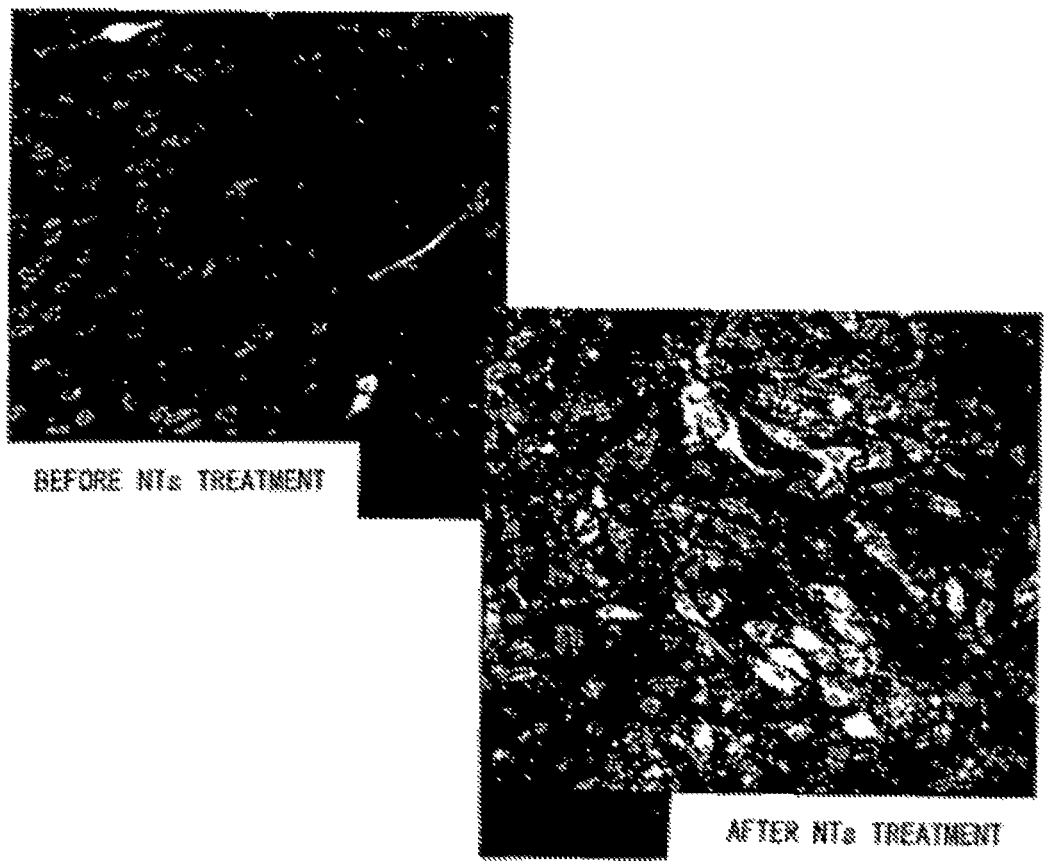
FIG. 6 is a pair of immunofluorescent photograph in lieu of a drawing, showing changes in the vesicular acetylcholine transporter positivity (rate of acetylcholinergic neuron differentiation) of neural cells induced to differentiate according to the invention, before and after treatment with neurotrophins (NTs; 2.5 S NGF).
Figure 7:
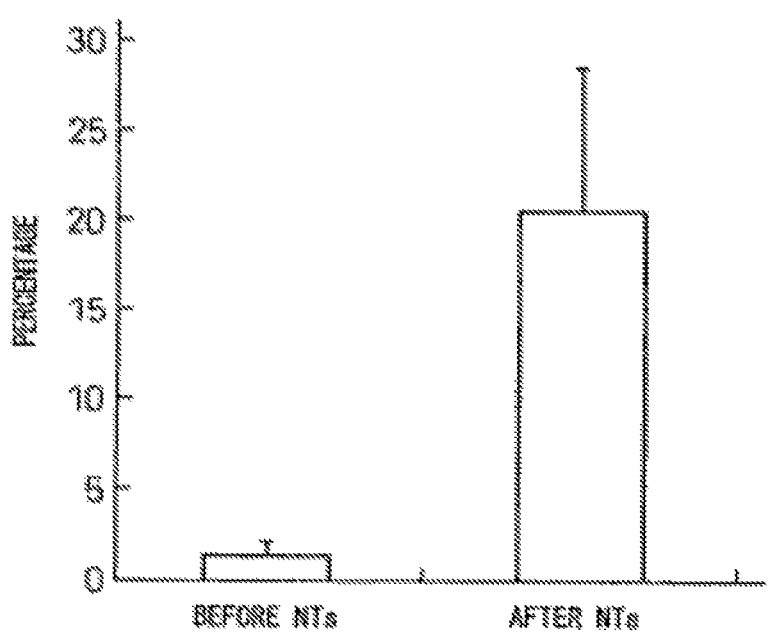
FIG. 7 is a graph showing changes in the vesicular acetylcholine transporter positivity (rate of acetylcholinergic neuron differentiation) of neural cells induced to differentiate according to the invention, before and after treatment with neurotrophins (NTs; 2.5 S NGF).

As a result of this procedure, the acetylcholinergic neurons exhibiting, reaction for vesicular acetylcholine transporter increased dramatically to 20.5±0.05% of the total neural cells (see right of graph in FIG. 7). As shown in the photograph of FIG. 6, the proportion of vesicular acetylcholine transporter protein stained green with FIPC increased dramatically after NGF (neurotrophin (NTs) treatment.

Example 4: Skeletal Muscle Induction

Stromal cells were extracted from the bone marrow of adult rats (Wistar rats) and cultured. The medium used was Minimum Essential Medium Alpha Eagle Modification (M4526, Sigma Co.) containing 20% fetal bovine serum (14-501F. Lot #61-1012, Bio Whittaker Co.).

After subculturing to four generations, 3 μmol/l of 5-azacytidine was added when the cells reached 80-90% confluence, and culturing was continued for 24 hours.

The medium was then switched with one containing 5 μM of forskolin (344273, Calbiochem), 10 ng/ml of basic fibroblast growth factor (100-18B, Peprotech EC, Ltd.) and 5 ng/ml of platelet-derived growth factor-AA (396-HB, Peprotech EC Ltd.) and 200 ng/ml of heregulin (396-HB, R&D Systems), and culturing was continued for another 7 days.

The Notch intracellular domain gene was then introduced in the same manner as Example 1.

On the day following introduction, G418 sulfate (83-5027, Gibco BRL) was added to a concentration of 200 ng/ml and introduced cells were selected for 10 days.

After restoration of the cell population to approximately 100% confluence, non-treated bone marrow stromal cells without the introduced gene were added to the medium and co-cultured therewith.

Figure 8:
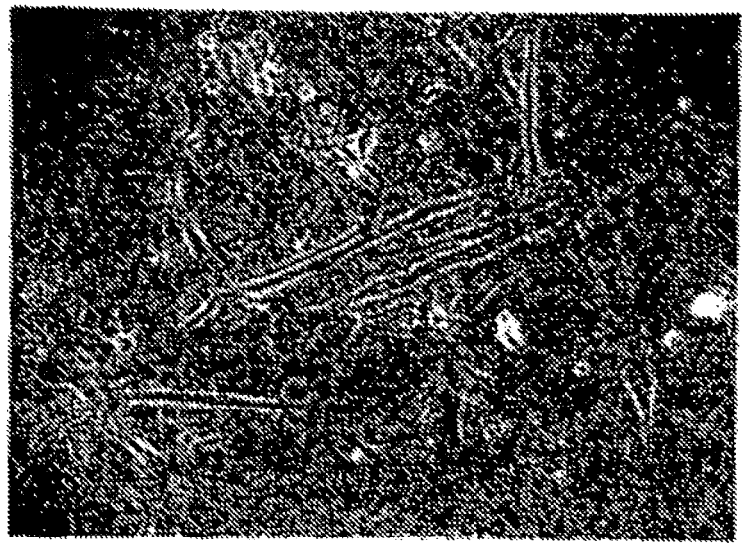
FIG. 8 is a micrograph (phase contrast microscope) in lieu of a drawing, showing skeletal muscle cells induced to differentiate according to the invention.
Figure 9:
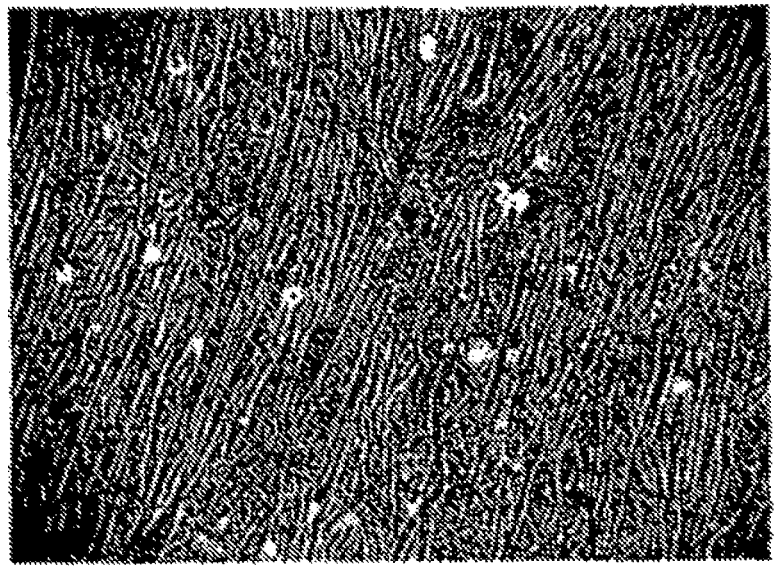
FIG. 9 is another micrograph (phase contrast microscope) in lieu of a drawing, showing skeletal muscle cells induced to differentiate according to the invention. This photograph shows the increase in the skeletal muscle of FIG. 8 with time.
Figure 10:
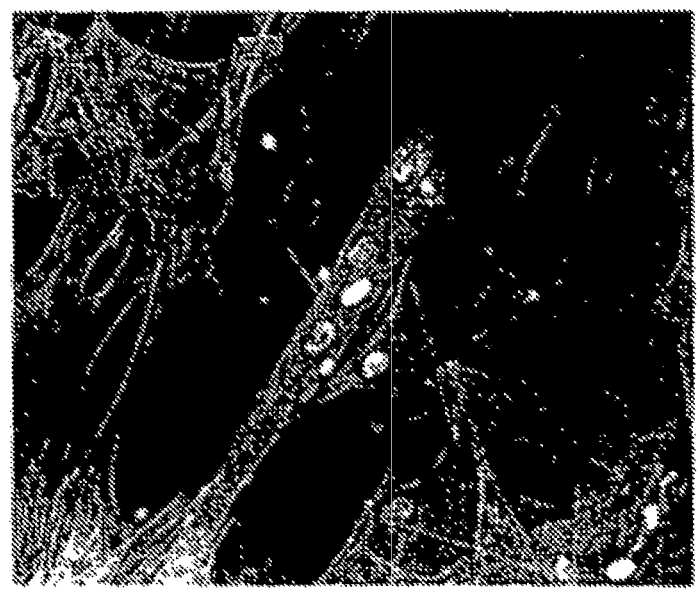
FIG. 10 is a confocal laser micrograph in lieu of a drawing, showing the polynucleated nature of skeletal muscle cells induced to differentiate according to the invention. The nuclei and the actin filaments can be seen.

After three days, 5 μM of forskolin (344273, Calbiochem) was added. After several more days, the cells fused into locally appearing polynucleated skeletal muscle cells (see FIG. 8), in an increasing manner with time (FIG. 9). The skeletal muscle cells were observed with a confocal laser microscope, as seen in FIG. 10. Expression of myogenin and Myf5 mRNA in the cells was confirmed by RT-PCR. Electron microscope observation revealed myofibers characteristic of skeletal muscle cells.

Example 5: Therapeutic Effect of Dopaminergic Neurons Obtained by Differentiation Inducing Method of the Invention when Transplanted into Striata of Rat Parkinson's Disease Models We examined the effect of transplanting dopaminergic neurons obtained by the differentiation inducing method of the invention into rat Parkinson's disease models. Injection of 6-0HDA (6-hydroxydopamine) into rat brain substantia nigra has already been established as a method of creating Parkinson's models, and these models were used for the present experiment (Svendsen et al., Exp. Neurol, 137:376-388(1996); Svensen et al., Exp. Neurol. 148:135-146 (1997)). Administration of apomorphine to such rat models is known to provoke rotational movement, with increasing rotations suggesting deterioration and reduced rotations suggesting improvement.

Figure 11:
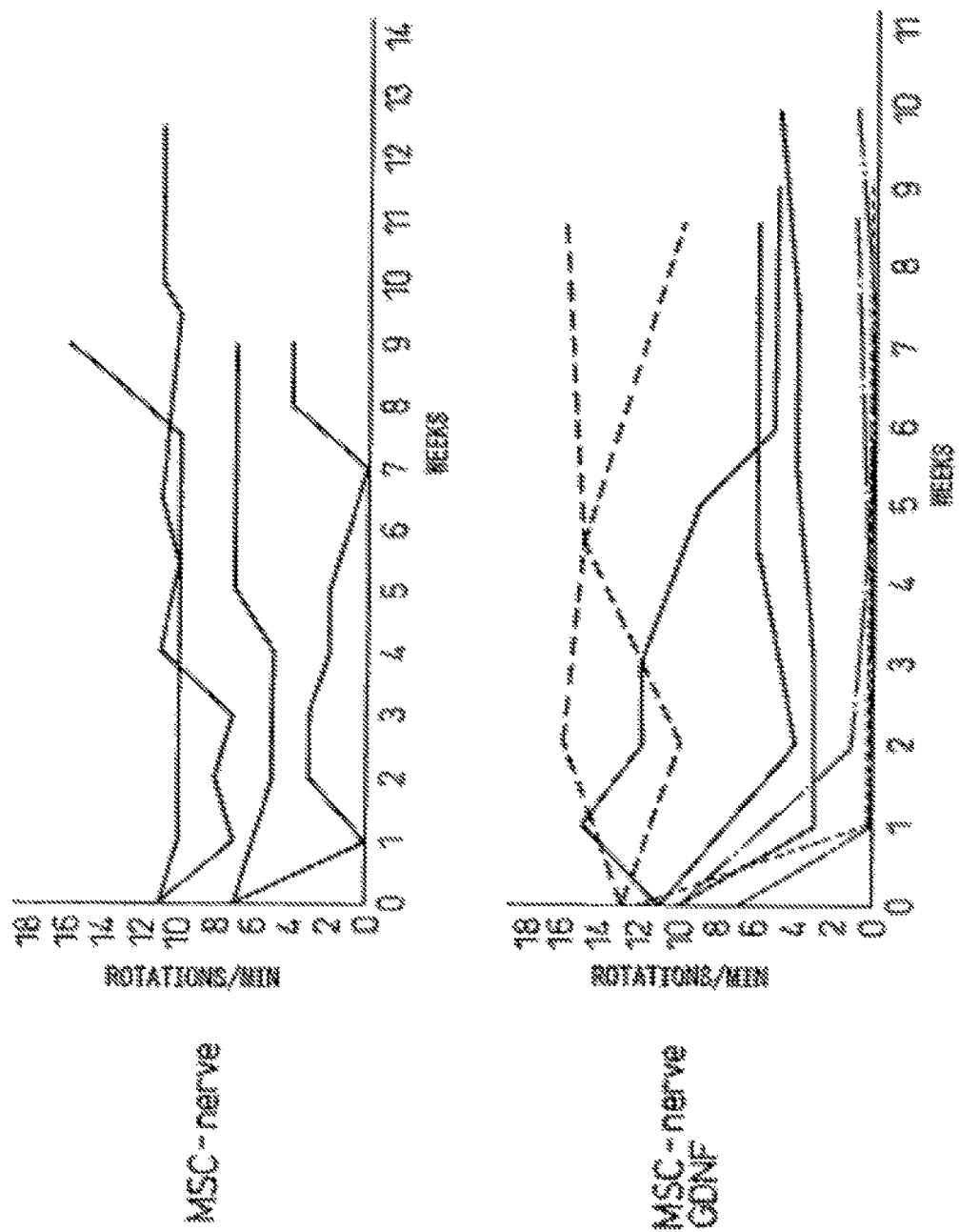
FIG. 11 is a pair of graphs showing the therapeutic effect of transplanting dopaminergic neurons obtained by the differentiation inducing method of the invention into striata of rat Parkinson's disease models.

As shown in the top graph of FIG. 11, with grafting of induced neural cells into striata, the number of rotations per minute during a 9-week observation period was approximately unchanged as compared to immediately after grafting. In the absence of treatment, the number of rotations per minute tended to gradually increase (not shown), and therefore the level slope indicated that at least aggravation was prevented.

As shown in the bottom graph of FIG. 11, with grafting of induced dopaminergic neurons into the striata, the number of rotations per minute began to decrease from the first week after grafting, and in approximately half of the animals, a very notable improvement was found with the number of rotations per minute reaching zero or only 1 or 2 after 9 weeks. (The two cases in the bottom graph of FIG. 11 which exhibited more than 8 rotations/minute after 9 weeks were thought to represent grafting failures and were excluded from the evaluation.)

In order to investigate the type of cells into which the dopaminergic neurons of the invention injected (grafted) into the striata had differentiated, the striatal tissue was extracted after 10 weeks and slices thereof subjected to an immunohistochemical examination.

The gene for green fluorescent protein (GFP) which emits green fluorescent light was incorporated into the chromosomes of bone marrow stromal cells using a retrovirus. Thus, as seen in the immunofluorescent photographs shown in FIG. 12, the neural cells induced to differentiate from bone marrow stromal cells, and therefore the dopaminergic neurons grafted into striata, emit green fluorescent light.

Also, red light emission was used for neurofilament as a marker for neural cells, tyrosine hydroxylase as a marker for dopaminergic neurons, GE AP as a marker for astrocytes (glial cells) and 04 as a marker for oligodendrocytes (glial cells).

Thus, superposition of green light by GFP and red light by the aforementioned markers produces yellow light, for distinction of the type of cells that the grafted dopaminergic neurons had become 10 weeks after grafting.

Figure 12:
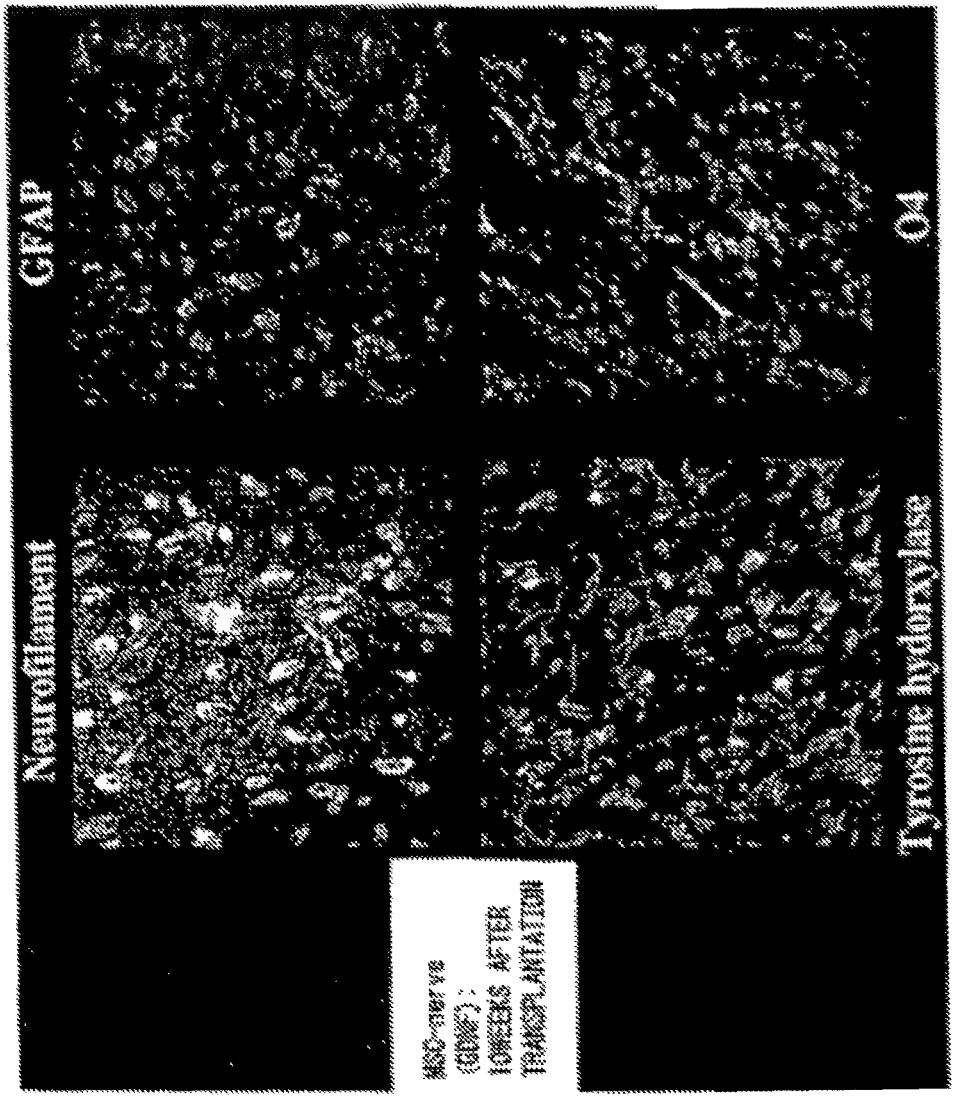
FIG. 12 is a composite of immunofluorescent photographs in lieu of a drawing, showing that the cells transplanted into the striata were not glial cells but neural cells and dopaminergic neurons.

As seen in FIG. 12, almost all of the striata-grafted cells had differentiated to neural cells but not to glial cells 10 weeks after grafting. Also, judging from the considerable number of tyrosine hydroxylase-positive neural cells (i.e. dopaminergic neurons), it is concluded that the in vitro differentiation inducing method of the present invention increased the proportion of dopaminergic neurons to 17.2±5.1% of the total neural cells, and that the aforementioned grafting further increased this proportion.

Figure 13:
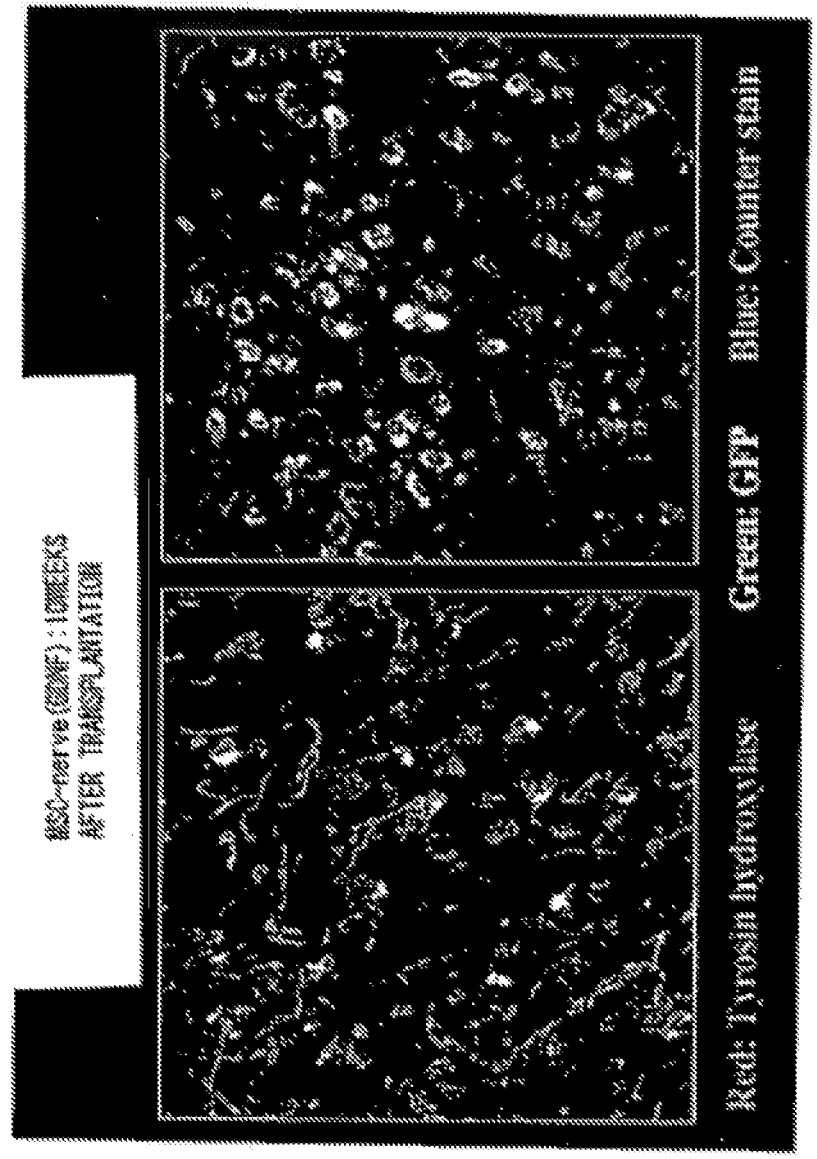
FIG. 13 is a composite of magnified immunofluorescent photographs in lieu of a drawing, showing that the cells transplanted into the striata were neural cells and dopaminergic neurons.

FIG. 13 is a composite of magnified immunofluorescent photographs showing coloration of tyrosine hydroxylase.

This procedure demonstrated that in these rat Parkinson's disease models, grafting of dopaminergic neurons obtained by the differentiation inducing, method of the invention into striata dramatically improved the symptoms of Parkinson's disease.

The following are the experimental protocols which were used in Examples 6 to 11 below.
Experimental Protocols
Culturing of Bone Marrow Stromal Cells Isolation of MSCs from Wistar rat bone marrow has been described in previous publications by the present inventors[4]. Human MSCs were obtained from a commercially available source (PT-2501, Bio Whittaker, Walkersville, Md.) and a healthy donor (obtained in conformity with the guidelines of the Ethics Committee of Kyoto University Graduate School of Medicine). The human MSCs were isolated by a previously described method[3]. The cells were cultured in alpha-MEM (M-4526, Sigma, St. Louis, Mo.) containing 10% fetal bovine serum (FBS).

FACS Analysis

Rat MSCs were incubated with FITC-labeled mouse anti-CD34 (Santa Cruz Biotechnology Inc., Santa Cruz, Calif.), anti-CD54, -CD90 and -CD11b/c or hamster anti-CD29 (PharMingen, San Diego, Calif.). Controls were incubated either with FITC labeled anti-mouse or anti-hamster IgG, or non-immune mouse serum. For human MSCs there were used phycoerythrin-labeled mouse anti-CD34, -CD29, -CD90, -CD54, -CD11c and -von Willebrand factor. Controls included cells stained with phycoerythrin-labeled anti-mouse IgG. The data were acquired and analyzed on FACScalibur with Cell Quest software (Becton Dickinson, Franklin Lakes, N.J.).
Plasmids Numbering of Notch1 was according to Weinmaster et al. (1991)39. cDNA for them-Notch 1 intracellular domain NICD (starting at amino acid 1703 and terminating at the 3' untranslated sequence), TM (amino acids 1747-2531), M2 (modified from TM by mutation of two amino acids Ala-Ala (1992 and 1993) to Glu-Phe) (NICD, TM and M2 provided by Dr. Masashi Kawaichi)[17,34], mNIC Δ3' (amino acids 1846-2477, provided by Dr. Jeffery Nye)[35], RAMIC (amino acids 1703-1969, obtained from NICD cDNA by digestion with Not1 and AccIII) and TADIC (amino acids 2192-2531, obtained from NICD cDNA by digestion with XhoI and XbaI) were subcloned into pCI-neo mammalian expression vector (Promega, Madison, Wis.). Luciferase reporter plasmids of 3-PGDH (both full length and M1965) were provided by Dr. Shigeki Furuya[19], NeuroD by Ming-Jer Tsai[40], and GF AP promoter by Caleb E Finch[41]. MSCs were transfected with these plasmids using lipofectamine 2000 (Invitrogen, Carlsbad, Calif.) and selected by G418 according to manufacturer's instruction.
Neural Induction Experiment For trophic factor induction, subconfluent cultures of NICD-transferred MSCs were incubated in alpha-MEM containing 10% FBS, 5 μM FSK (Calbiochem, La Jolla. Calif.), 10 ng/ml bFGF (Peprotech, London, UK) and 10 ng/ml CNTF (R&D Systems, Minneapolis, Minn.). For GDNF treatment, 50 ng/ml of GDNF (Peprotech) was administered into alpha-MEM culture medium containing 10% FBS.
Brd-U Labeling After trophic factor induction (5 days), Brd-U (10 μM) was added to the culture medium and culturing was carried out for 24 hours. Cells were then fixed with 4% paraformaldehyde in PBS and double labeled for MAP-2ab and Brd-U, prior to TOT0-3 (Molecular Probes) counter staining.
RT-PCR Analysis Total cellular RNA was isolated using an SV total RNA isolation system (Promega). To analyze relative expression of different mRNAs, the amount of cDNA was normalized based on the signal from ubiquitously expressed β-actin mRNA. PCR was performed using standard protocols with Taq polymerase (Sigma). Cycling parameters were denaturation at 94° C. for 30 sec, annealing at 54-68° C. for 1 min depending on the primer, and elongation at 72° C., with 35 cycles.
Immunocytochemistry The specific procedure has been previously described[4]. Antibodies to GLAST were provided by Dr. Masahiko Watanabe[18], and 3-PGDH by Dr. Shigeki Furuya[19]. The following primary antibodies were purchased commercially: nestin (1:500, PharMingen), MAP-2ab (1:250, Sigma), neurofilament-M (1:200, Chemicon, Temecula, Calif.), β-tubulin isotype 3 (1:400, Sigma), TuJ-1 Babco, Richmond, Calif.), GFAP (1:1, DAKO, Carpinteria, Calif.), 04 (1:20, Boehringer Mannheim, Germany), GalC (1:30, Chemicon), GABA (1:1000, Sigma), serotonin transporter (1:200, Chemicon), vesicular acetylcholine transporter (1:100, Chemicon), glutamine (1:100, Chemicon), neuropeptide Y (1:1000, Peninsula Laboratories Inc., Belmont, Calif.), TH (1:200, Chemicon), VIP b: 500, Incstar, Stillwater, Minn.), CGRP (1:1200, Amersham, Buckinghamshire, UK), SP (1:500, Amersham), DAT (1:200, Chemicon). Cells were incubated with Alexa Fluor 488- or 546-conjugated secondary antibodies, and TOTO-3 iodide counter staining was performed. The cells were examined under a confocal laser scanning microscope (Radians 2000, Bio-Rad, Hertfordshire, U K).

Reporter Assays

Cells were transfected using lipofectamine 2000 (Invitrogen) according to the manufacturer's instruction. Forty-eight hours after transfection, cells were assayed for Firefly and Renilla luciferase activities using a dual luciferase assay kit (Promega). Firefly luciferase values were corrected for transfection efficiency by including plasmids expressing Renilla luciferase.

Western-Blot Analysis.

Cell lysates were prepared and 50 µg of lysate proteins were electrophoresed on 5% and 10% SDS-polyacrylamide gel. Antigens to MAP-2 (1:500, Chemicon), GF AP (1:500, Dako) and TH (1:1000, Chemicon) antibodies were detected using alkaline phosphatase.

Electrophysiological Methods

Currents were measured at room temperature (20-25° C.) with a CEZ-2300 (Nihon Kohden, Tokyo, Japan) patch-clamp amplifier. Data acquisition and stimulation were controlled with the pClamp 6.0 software (Axon Instruments, Inc., Foster City, Calif.). Signals were filtered at 5 kHz. and sampled at 10-50 kHz. Experiments were performed in a whole-cell patch-clamp configuration using pipettes (borosilicate glass, Narishige, Tokyo, Japan) with resistance values in the range of 4-8 MΩ. For recording of delayed rectifier potassium currents, the standard extracellular solution contained (mM) NaCl (150), KCl (4), CaCh (2), MgCh (2), glucose (10) and Hepes (10) (pH 7.4 with NaOH). The standard pipette solution was (mM) KCl (130) MgCh (5), EGTA (10), and Hepes (10) (pH 7.4 with KOH).

Analysis of Parkinson Disease Model Rats

A procedure for creating this disease model has been described in a previous report[45]. In brief, adult male Wistar rats (weighing 250-300 g) were anesthetized with sodium pentobarbital (40 mg/kg, intraperitoneal), and then 6-OHDA solution (8 µg/4 µl of 0.1% ascorbate-saline) was injected into the left medial forebrain bundle (A/P=−4.4 mm; L=+1.1 mm from bregma, V=−7.7 mm from dura).

Prolonged contralateral rotation was used as a target behavior, and rats showing an average of fewer than 6 rotations per minute for the first 30 minutes after apomorphine administration (0.8 mg/Kg, subcutaneous) were excluded. 1×10$^5$ cells/8 µl were grafted into the lesioned striatum at the following coordinates: A/P=+0.5 mm; L=+3.0 mm from bregma, and V=−4.5 mm. The number of animals were 5 in the MSC group, 6 in the N-MSC group and 10 in the G-MSC group.

For immunohistochemistry of grafted striata (G-MSC group 10 weeks postoperation), glia sections were incubated with antibodies against neurofilament-M, TH, DAT, GF AP and 04. These were then detected by Alexafluor 546-labeled secondary antibodies (Molecular Probes), prior to TOTO-3 iodide counter staining.

For human MSC transplantation, 5 animals were grafted and immunosuppressed by subcutaneous injection of FK506 (1 mg/kg, Fujisawa, Osaka, Japan) once a day. Four weeks after transplantation, apomorphine induced rotation was measured. For dopamine measurement in HPLC, 1 mm thick coronal brain slices were obtained (A/P+2.5 mm to −1.5 mm from bregma; 4 slices total), separated at the midline, and each side was cultured separately in alpha-MEM containing 10% FBS. After 24 hours, the culture media were collected and provided for HPLC analysis by SRL Communication and Health, Tokyo, Japan. All animal experiments were approved by the Animal Care and Experimentation Committee of Kyoto University Graduate School of Medicine.

Statistical Analysis

Data were expressed as mean±SEM, Data were compared using ANOVA with pairwise comparisons by the Bonferroni method. P values of <0.05 were regarded as significant, and <0.01 as highly significant.

Example 6: Identification of MSCs

The rat and human MSCs were used for the next experiment. The rat MSCs (Wistar) were isolated by a previously described method and cultured[4]. The human MSCs were obtained from a healthy donor or purchased from a commercial source (Bio Whittaker).

The cell surface markers were evaluated on the rat MSCs and human MSCs using fluorescent activated cell sorting (FACS). The MSCs expressed CD29 (β1-integrin), CD90 (Thy-1) and CD54 (ICAM-1), but not CD34 (hemopoietic stem cell marker), CD11 b/c (macrophage-related marker) or von Willebrand factor (human endothelial cell marker, data not shown) (FIG. 14a). This result matched previous reports[3, 11]. Similar results were obtained by immunocytochemical examination (FIGS. 14b-f). Lipogenic, chondrogenic and osteogenic differentiation from both the rat and human MSCs were confirmed according to the method described in Pittenger et al. (1999)[3]. This indicated that the cells were a mesenchymal source (data not shown).

Example 7: Effect of NICD Transfection on MSCs

NICD was transfected into the MSCs, since Notch signaling activity is found in the intracellular domain of the Notch protein and deletions that remove the extracellular domain can elicit a constitutively active form of Notch[16]. NICD comprises a sequence coding for a small extracellular domain portion, the transmembrane region and the entire intracellular domain of mouse Notch[17], and was provided by Dr. Kawaichi of the Nara Institute of Science and Technology. The fragment was subcloned into pCI-neo, a mammalian expression vector containing the CMV promoter, and then transfected into the MSCs by lipofection and subsequent selection of G418.

Figure 15A:
Figure 15B:
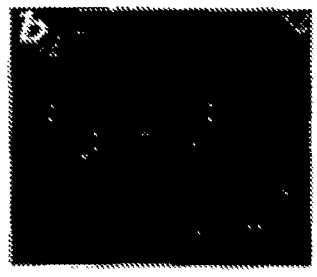
Figure 15C:
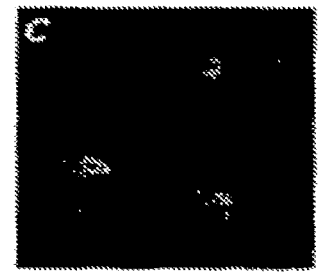
Figure 15D:
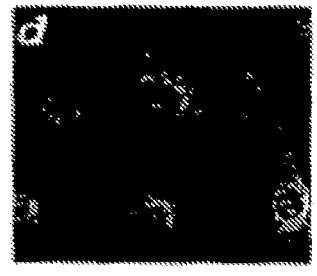
Figure 15E:
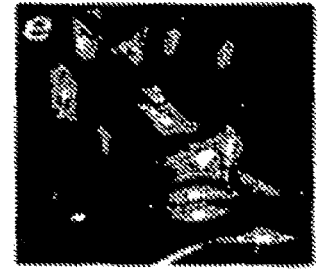
Figure 15F:
Figure 15G:

Since the Notch extracellular and intracellular domains were detected, the non-treated MSCs expressed small amounts of endogenous Notch. However, the NICD transfected MSCs predominantly expressed only NICD and the extracellular domain was not detected (FIG. 15a).

The glutamate transporter GLAST and 3-phosphoglycerate dehydrogenase (3PGDH) are present in neural stem cells (NSC) and radial glia[18,19]. These are thought to be lineally related to stem cells, and may serve as a source of neurons during embryogenesis[20]. Bromodeoxyuridine (Brd-U)-positive NSCs in the dentate gyrus of adult mouse hippocampus were almost invariably immunopositive for 3PGDH[19]. After transfection of NICD, the rat MSCs unregulated transcription and expression of both of these molecules as well as nestin, a known marker for NSC and neural progenitor cells (NPC)[21]. The non-treated MSCs exhibited almost no expression of GLAST or 3PGDH, but a very small fraction of cells were positive for nestin (0.74±0.1%). After NICD transfection, however, these cells unregulated GLAST, 3PGDH and nestin (4.92±1.0%, p<0.01) (FIGS. 15b-g). In a luciferase promoter assay, 5'-flanking full length (nucleotides-3472 to −1) and 5'-flanking M1965 (−1792 to −1) 3PGDH activities (both reported to be active in radial glia and neuroepithelial stem cells[19] were significantly increased in the rat MSCs after NICD transfection (p<0.01) (FIG. 15h). (The promoters were provided by Dr. S. Furuya, Brain Science Institute, RIKEN).

In vertebrates, NSC and neural crest stem cells adopt a glial fate through inhibition of neural differentiation[13,14,16]. The present inventors have confirmed that insertion of NICD into rat NSCs generates GFAP-positive astrocytes, but very few GFAP-positive cells were discovered in the NICD-transfected MSCs (data not shown). On the other hand, it has been reported that introduction of activated Notch1 into mouse forebrain promotes radial glia identity during embryogenesis[15]. Since the MSCs expressed NSC and NPC related markers after introduction of NICD, it is plausible that NICD transfection caused the MSCs to change their phenotype to one resembling NSCs and/or NPCs.

Neural Induction in NICD-Transfected MSCs

The present inventors investigated the conditions necessary to selectively generate neural cells from NICD-transfected MSCs. We therefore tested various factors known to act on neurogenesis[22] (neurotrophins, leukemia inhibitory factor, bFGF and CNTF) and forskolin. We found that the most efficient condition for specific induction of neural cells was simultaneous introduction of FSK, bFGF and CNTF. (Hereinafter referred to as "trophic factor introduction" throughout the present specification.)

Figure 16:
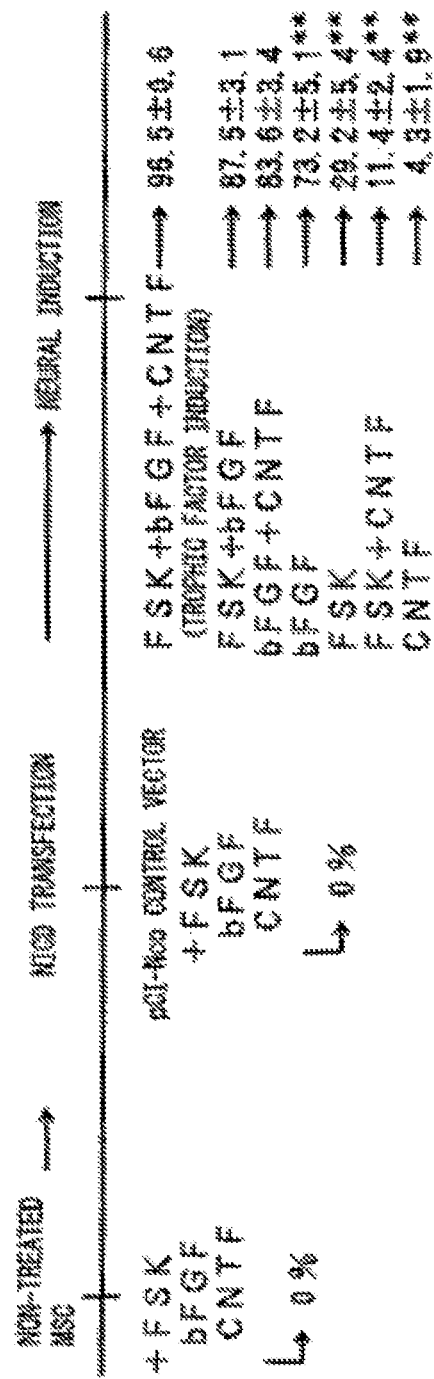
FIG. 16 shows the rates of conversion to MAP-2ab+ cells upon treatment with various trophic factors. No MAP-2ab+ cells were detected when the trophic factors were introduced into rat MSCs either non-treated or transfected with a control vector. Introduction of three of the trophic factors (FSK+6FGF+CNTF) showed the highest rate of neural cell production (96.5%), while elimination of any of these three factors resulted in a lower conversion rate.

Following NICD transfection into rat MSCs, culturing of the cells to 60-70% confluence and introduction of three trophic factors (FSK±pFGF±CNTF), 96.5±0.6% of the cells were MAP-2ab positive after 5 days (FIG. 16, FIGS. 17a-d). The present inventors observed MAP-2ab-positivity rates of 73.2±5.1% with bFGF alone and 87.5±3.1% and 83.6±3.4% when FSK and CNTF were also added. This difference was not significant (p>0.05)(FIG. 16). FSK and CNTF respectively produced rates of 29.2±5.4 and 4.3±1.9% alone (p<0.01) and 11.4±2.4% together (FIG. 16).

The induction of MAP-2ab cells by trophic factors was most likely caused by inhibition of glial and other cell differentiation from MSCs rather than by specific killing of non-neural cells, because almost no dead cells were observed by TOTO-3 nuclear staining following trophic factor induction (data not shown).

Trophic factor induction by itself, or after insertion of a pCI-neo control vector without NICD, resulted in no recognizable neural phenotypes (FIG. 16). Therefore it would seem that NICD transfection is critical for neural induction of MSCs.

Characterization of MSC Neural Cells

Neural cells derived from the aforementioned rat and human MSCs showed distinct morphological features characteristic of neurons, including neurite-like processes with abundant varicosities, and expressed typical neural markers such as neurofilament-M, β3-tubulin and Tuj1 (FIGS. 17a~g). Nestin-positive cells, though few, could also be recognized (2.03±0.7%)(data not shown). Induced neural cells were unable to proliferate when subcultured after trypsin treatment. Brd-U incorporation studied 5 days after trophic factor induction showed minimal labeling of MAP-2ab positive cells (FIG. 17h), suggesting that these neural cells are mitotically terminated.

MAP-2ab was not detected by Western blotting in non-treated MSCs but was found after trophic factor induction (FIG. 17l(1)).

A developmental rise in delayed rectifier potassium current is associated with the maturation of cell excitability and neural differentiation[23]. The present inventors investigated this property in the induced neural cells by using the voltage clamp method. An outwardly rectified K+ current was elicited by positive voltage steps in induced MSCs derived from both rats and humans. The amplitude of this current was dramatically higher than that in non-treated MSCs (FIGS. 17m-q). The present inventors also investigated resting membrane potential under current clamp conditions immediately after whole-cell configuration was formed. Resting membrane potentials were lower among neural cells than in non-treated MSCs (−50 to +60 mV and −30 to −40 mV respectively). These neurophysiological properties induced in MSCs resemble those of mature neurons.

In checking for glial cells, the present inventors performed immunocytochemistry using GFAP as a marker for astrocytes, and galactocerebroside (GalC) and 04 as markers for oligodendrocytes. No marker-positive glial cells were detected after trophic factor induction of rat or human MSCs (FIGS. 17i-k). This was confirmed by Western blotting (FIG. 17l(2)). To further confirm specificity of neural induction, the present inventors measured the promoter activities of NeuroD and GFAP. In non-treated rat MSCs, the rates for NeuroD and GFAP were 67.2±15.3 and 5.16±1.36, respectively. Following trophic factor induction, however, NeuroD activity increased significantly to 132.7±20.9 while GFAP decreased to 0.63±0.22 (FIG. 18). These results indicate that only neural cells were specifically induced from NICD-transfected MSCs after trophic factor induction.

Generation of TH-Positive Cells

Figure 19A:
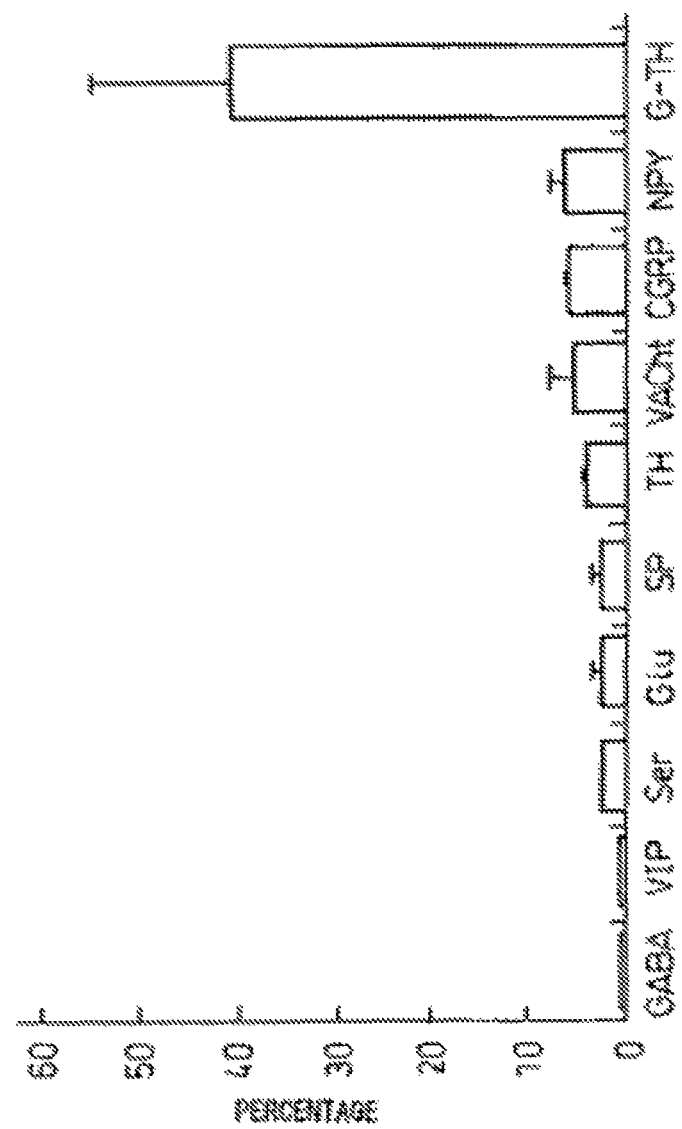
Figure 19G:
Figure 19H:
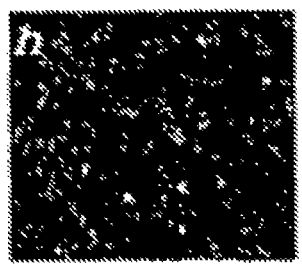
Figure 19I:
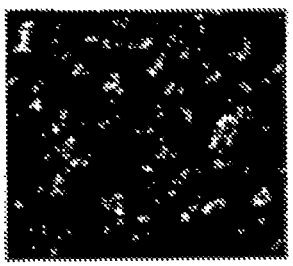
Figure 19J:
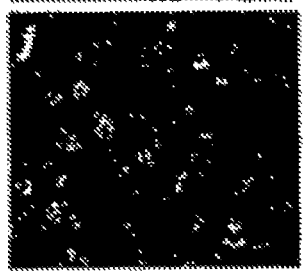
Figure 19K:

Neural function is closely related to cell type-specific neurotransmitters. The present inventors therefore performed immunocytochemical examination of neurotransmitters and related proteins after trophic factor induction (FIG. 19a). GDNF is known to be involved with the generation and development of midbrain dopaminergic neurons[36]. The present inventors also examined whether administration of GDNF induces neural MSCs to increase their proportion of tyrosine hydroxylase (TH)-positive cells. This percentage increased from 3.9±0.6% after trophic factor induction alone up to 41.0±14.1% following administration of GDNF (FIG. 19a~c). GDNF also induced expression of Nurr-1, which is a transcription factor that has a role in the differentiation of midbrain precursors into dopaminergic neurons[37] (FIG. 19d). Western blotting further confirmed these results (FIG. 19e).

Transplantation of Neural Cells to Parkinson's Disease Model Rats

In order to explore the ability of MSC derived neural cells to survive and function in vivo, both rat and human cells were transplanted into the striata of Parkinson's disease model rats. Unilateral administration of 6-0HDA into the medial forebrain bundle selectively destroys dopaminergic neurons in the substantia nigra, thus providing a useful model of Parkinson's disease. Three types of rat MSCs labeled with green fluorescent protein (GFP)[4] were transplanted: 1) non-treated (MSC group), 2) after trophic factor induction into neural cells (N-MSC group), and 3) GDNF administration after induction (GMSC group). Animals received implantation of 1×10$^5$ MSCs ipsilateral to the lesioned striatum. Apomorphine-induced rotational behavior was examined for 10 weeks following cell implantation. The MSC group showed a rotational bias away from the lesioned side which persisted, whereas the N-MSC group showed slight recovery over time. In contrast, the G-MSC group demonstrated significant recovery from rotation behavior (FIG. 19f). The transplanted animals were followed up to 16 weeks, with no tumor formation observed in the brain.

Ten weeks following grafting the brains were examined histologically, including immunohistochemistry. Grafted striata showed GFP-positive cells, while transplanted cells were positive for neurofilament and, in a few cases, showed labeling with anti-GFAP or anti-O4 antibodies. Many of the transplanted cells were also positive for TH and dopamine transporter (DAT)(FIGS. 19g~k). The percentage of GFAP-positive cells among GFP-labeled MSCs was 2.5±1.4%, while the percentages of TH- and DAT-positive cells were 45.7±4.2% and 30.7±0.9%, respectively. In serial sections of the G-MSC group, grafted cells were found to migrate and extend into the host striatum (FIG. 19l). Approximately $3.4 \times 10^4$ cells (34%) were counted in the striatum.

Human GDNF-treated neural MSCs were similarly transplanted into the striata of 6-OHDA-lesioned rats. The animals were immunosuppressed with FK 506 daily, and rotation behavior was recorded at 4 weeks. Grafting resulted in significant improvement in rotational behavior (mean rotation index, post/pre-operation, was 0.44±0.2)(FIG. 19m). The capacity of grafted human MSCs to synthesize and release dopamine was assessed by measuring dopamine concentration in the culture medium of slices of transplanted brain by high-performance liquid chromatography (HPLC). Brain slices were separated at the midline into grafted and intact sides and cultured separately. The dopamine concentration in the culture medium from each side was measured and the ratio of lesioned to intact side was calculated. Sham-operated rats showed a ratio of 0.57±0.01 (n=3) in contrast to the grafted animals' ratio of 0.67±0.04 (n=3). This was consistent with an increase in dopamine release (p=0.04) with transplantation. These results suggest that neural cells induced from human MSCs were able to synthesize and release dopamine in lesioned rat striata.

REFERENCES

Bishop, A. E., Buttery, L. D. & Polak, J. M. Embryonic stem cells (Review). J. Pathol. 197, 424-429 (2002).
Weissman, L L. Stem cells: units of development, units of regeneration, and units in evolution (Review). Cell 100, 157-168 (2000).
Pittenger, M. F. et al. Multilineage potential of adult human mesenchymal stem cells. Science 284, 143-147 (1999).
Dezawa, M. et al. Sciatic nerve regeneration in rats induced by transplantation of in vitro differentiated bone-marrow stromal cells. Eur. J. Neurosci. 14, 1771-1776 (2001).
Jiang, Y. et al. Pluripotency of mesenchymal stem cells derived from adult marrow. Nature 418, 41-49 (2002).
Eglitis, M. A., Dawson, D., Park, K. W. & Mouradian, M. M. Targeting of marrow-derived astrocytes to the ischemic brain. Neuroreport 10, 1289-1292 (1999).
Kopen, G. C., Prockop, D. J. & Phinney, D. G. Marrow stromal cells migrate throughout forebrain and cerebellum, and they differentiate into astrocytes after injection into neonatal mouse brains. Proc. Natl. Acad. Sci. USA 96, 10711-10716 (1999).
Terada, N. et al. Bone marrow cells adopt the phenotype of other cells by spontaneous cell fusion. Nature 416, 542-545 (2002).
Wagers, A. J., Sherwood, R. L. Christensen, J. L. & Weissman, LL. Little evidence for developmental plasticity of adult hematopoietic stem cells. Science 297, 2256-2259 (2002).
Woodbury, D., Schwarz, E. J., Prockop, D. J. & Black, LB. Adult rat and human bone marrow stromal cells differentiate into neurons. J. Neurosci, Res. 61, 364-370 (2000).
Kohyama, J. et al. Brain from bone: efficient "meta-differentiation" of marrow stroma-derived mature osteoblasts to neurons with Noggin or a demethylating agent. Differentiation 68, 235-244 (2001).
Sanchez-Ramos, J. R. Neural cells derived from adult bone marrow and umbilical cord blood. J. Neurosci. Res. 69, 880-893 (2002).
Lundkvist, J. & Lendahl, U. Notch and the birth of glial cells (Review). Trends Neurosci. 24, 492-494 (2001).
Morrison, S. J. et al. Transient Notch activation initiates an irreversible switch from neurogenesis to gliorenesis by neural crest stem cells. Cell 101, 499-510 (2000).
Gaiano, N., Nye, J. S. &. Fishell G. Radial glial identity is promoted by Notch1 signaling in the murine forebrain. Neuron 26, 395-404 (2000).
Nye, J. S., Kopan, R. & Axel, R. An activated Notch suppresses neurogenesis and myogenesis but not gliogenesis in mammalian cells. Development 120, 2421-2430 (1994).
Yamamoto, N. et al. Role of Deltex-1 as a transcriptional regulator downstream of the Notch receptor. J. Biol. Chem. 276, 45031-45040 (2001).
Shibata, T. et al. Glutamate transporter GLAST is expressed in the radial glia-astrocyte lineage of developing mouse spinal cord. J. Neurosci. 17, 9212-9219 (1997).
Yamasaki, M. et al. 3-Phosphoglycerate dehydrogenase, a key enzyme for 1-serine biosynthesis, is preferentially expressed in the radial glia/astrocyte lineage and olfactory ensheathing glia in the mouse brain. J. Neurosci. 21, 7691-7704 (2001).
Gregg, C. T., Chojnacki, A. K. & Weiss, S. Radial glial cells as neural precursors: the next generation? J. Neurosci. Res. 69, 708-713 (2002).
Roy, N. S. et al. In vitro neurogenesis by progenitor cells isolated from the adult human hippocampus. Nat. Med. 6, 271-277 (2000).
Ip, N. Y. The neurotrophins and neuropoictic cytokines: two families of growth factors acting on neural and hematopoietic cells (Review). Ann. N. Y. Acad. Sci. 840, 97-106 (1998).
Grosse, G. et al. Expression of Kv1 potassium channels in mouse hippocampal primary cultures: development and activity-dependent regulation. J. Neurosci. 20, 1869-1882 (2000).
Morrison, S. J. Neural differentiation: proneural genes inhibit gliogenesis (Review). Curr. Biol. 11, R349-351 (2001).
Sun, Y. et al. Neurogenin promotes neurogenesis and inhibits glial differentiation by independent mechanisms. Cell 104, 365-376 (2001).
Ishibashi, M. et al. Persistent expression of helix-loop-helix factor HES-1 prevents mammalian neural differentiation in the central nervous system. EMBO J. 13, 1799-1805 (1994).
Furukawa, T. et al. rax, Hes1, and notch1 promote the formation of Muller glia by postnatal retinal progenitor cells. Neuron 26, 383-394 (2000).
Seidel, H. M., Lamb, P. & Rosen, J. Pharmaceutical intervention in the JAK/STAT signaling pathway (Review). Oncogene 19, 2645-2656 (2000).

Burdon, T., Smith, A. & Savatier, P. Signalling, cell cycle and pluripotency in embryonic stem cells. Trends Cell Biol. 12, 432-438 (2002).

Nakashima, K. et al. BMP2-mediated alteration in the developmental pathway of fetal mouse brain cells from neurogenesis to astrocytogenesis. Proc. Natl. Acad. Sci. USA. 98, 5868-5873 (2001).

Stork, P. J. & Schmitt, J. M. Crosstalk between cAMP and MAP kinase signaling in the regulation of cell proliferation. Trends Cell Biol. 12, 258-266 (2002).

Neufeld, B. et al. Serine/Threonine kinases 3pK and MAPK-activated protein kinase 2 interact with the basic helix-loop-helix transcription factor E47 and repress its transcriptional activity. J. Biol. Chem 275, 20239-20242 (2000).

Shimazaki, T., Shingo, T. & Weiss, S. The ciliary neurotrophic factor/leukemia inhibitory factor/gp130 receptor complex operates in the maintenance of mammalian forebrain neural stem cells. J. Neurosci. 21, 7642-7653 (2001).

Kurooka, H., Kuroda, K. & Honjo, T. Roles of the ankyrin repeats and C terminal region of the mouse notch1 intracellular region. Nucleic Acids Res. 26, 5448-5455 (1998).

Franklin, J. L. et al. Autonomous and non-autonomous regulation of mammalian neurite development by Notch1 and Delta1. Curr. Biol. 9, 1448-1457 (1999).

Akerud, P. et al. Differential effects of glial cell line-derived neurotrophic factor and neurturin on developing and adult substantia nigra dopaminergic neurons. J. Neurochem. 73, 70-78 (1999).

Sakurada, K., Ohshima-Sakurada, M., Palmer, T. D. & Gage. F. H. Nurr1, an orphan nuclear receptor, is a transcriptional activator of endogenous tyrosine hydroxylase in neural progenitor cells derived from the adult brain. Development 126, 4017-4026 (1999).

Kim, J. H. et al. Dopamine neurons derived from embryonic stem cells function in an animal model of Parkinson's disease. Nature 418, 50-56 (2002).

Weinmaster, G., Roberts, V. J. & Lemke, G. A homolog of *Drosophila* Notch expressed during, mammalian development. Development 113, 199-205 (1991).

Peyton, M. et al. BETA3, a novel helix-loop-helix protein, can act as a negative regulator of BETA2 and MyoD-responsive genes. Mol. Cell Biol. 16, 626-33 (1996).

Rozovsky, I. et al, Estradiol (E2) enhances neurite outgrowth by repressing glial fibrillary acidic protein expression and reorganizing laminin. Endocrinology 143, 636-646 (2002).

Seta, Y., Toyono, T., Takeda, S. & Toyoshima, K. Expression of Mash1 in basal cells of rat circumvallate. taste buds is dependent upon gustatory innervation. FEBS Lett. 444, 43-46 (1999).

Schwalger, F. W. et al. Peripheral but not central axotomy induces changes in Janus kinases (JAK) and signal transducers and activators of transcription (STAT). Eur. J. Neurosci. 12, 1165-1176 (2000).

Kawasaki. H. et al. Induction of midbrain dopaminergic neurons from ES cells by stromal cell-derived inducing activity. Neuron 28, 31-40 (2000).

Tanaka, H. et al. Role of serotonergic neurons in L-DOPA-derived extracellular dopamine in the striatum of 6-0HDA-lesioned rats. Neuroreport 10, 631-634 (1999).

We claim:

1. A method for producing a composition in vitro, the method comprising combining neural precursor cells with a pharmaceutically acceptable carrier or excipient, wherein the neural precursor cells are obtained by a method comprising:
   (a) culturing bone marrow stromal cells (BMSCs) in a culture medium;
   (b) introducing, into the BMSCs of step (a), a nucleic acid comprising sequences encoding the intracellular domain of the Notch protein, wherein said sequences do not encode a full-length Notch protein;
   (c) selecting cells that comprise the nucleic acid of step (b); and
   (d) further culturing the selected cells of step (c) in the absence of selection, to obtain neural precursor cells (NPCs) expressing GLAST glutamate transporter, 3-phosphoglycerate dehydrogenase (3-PDGH) and nestin.

2. The method of claim 1, wherein the composition is a pharmaceutical composition for treatment of a disease, disorder or condition of the central nervous system.

3. The method of claim 2, wherein the disease, disorder or condition of the central nervous system is selected from the group consisting of spinal damage, cerebrovascular impairment, and a neurodegenerative condition.

4. The method of claim 2, wherein the disease, disorder or condition occurs in a human.

5. The method of claim 1, wherein the BMSCs are obtained from a human.

6. A method for producing a composition in vitro, the method comprising combining neural precursor cells with a pharmaceutically acceptable carrier or excipient, wherein the neural precursor cells are obtained by a method comprising:
   (a) culturing BMSCs in a culture medium;
   (b) introducing, into the BMSCs of step (a), a nucleic acid comprising sequences encoding the intracellular domain of the Notch protein;
   (c) selecting cells that comprise the nucleic acid of step (b); and
   (d) further culturing the selected cells of step (c) in the absence of selection, to obtain neural precursor cells (NPCs) expressing GLAST glutamate transporter, 3-phosphoglycerate dehydrogenase (3-PDGH) and nestin, wherein said NPCs do not express exogenous Notch extracellular domain.

7. The method of claim 6, wherein the composition is a pharmaceutical composition for treatment of a disease, disorder or condition of the central nervous system.

8. The method of claim 7, wherein the disease, disorder or condition of the central nervous system is selected from the group consisting of spinal damage, cerebrovascular impairment, and a neurodegenerative condition.

9. The method of claim 7, wherein the disease, disorder or condition occurs in a human.

10. The method of claim 6, wherein the BMSCs are obtained from a human.

* * * * *